US011446487B2

(12) United States Patent
Wong et al.

(10) Patent No.: US 11,446,487 B2
(45) Date of Patent: Sep. 20, 2022

(54) SYSTEM AND METHODS FOR CANCER TREATMENT USING ALTERNATING ELECTRIC FIELDS

(71) Applicant: Beth Israel Deaconess Medical Center, Inc., Boston, MA (US)

(72) Inventors: Eric Wong, Milton, MA (US); Edwin Lok, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/335,920

(22) PCT Filed: Sep. 22, 2017

(86) PCT No.: PCT/US2017/053051
§ 371 (c)(1),
(2) Date: Mar. 22, 2019

(87) PCT Pub. No.: WO2018/057953
PCT Pub. Date: Mar. 29, 2018

(65) Prior Publication Data
US 2019/0314631 A1    Oct. 17, 2019

Related U.S. Application Data

(60) Provisional application No. 62/399,301, filed on Sep. 23, 2016.

(51) Int. Cl.
*A61N 1/36* (2006.01)
*G16H 20/40* (2018.01)
(Continued)

(52) U.S. Cl.
CPC ....... *A61N 1/36002* (2017.08); *A61N 1/0456* (2013.01); *A61N 1/0476* (2013.01);
(Continued)

(58) Field of Classification Search
CPC .............. A61N 1/36002; A61N 1/0456; A61N 1/0476; A61N 1/08; A61N 1/36;
(Continued)

(56) References Cited

U.S. PATENT DOCUMENTS 8,494,627 B2 * 7/2013 Bikson .................. G16H 50/50
607/2
2010/0030211 A1 * 2/2010 Davalos ................. A61N 1/327
606/41

(Continued)

FOREIGN PATENT DOCUMENTS

| WO | WO 2010/120823 A2 | 10/2010 |
| WO | WO 2015/142922 A1 | 9/2015 |
| WO | WO 2017/072706 A1 | 5/2017 |

OTHER PUBLICATIONS

The electric field distribution in the brain, Wenger et al., 2015; https://www.ncbi.nlm.nih.gov/pmc/articles/PMC4628548/pdf/nihms723452.pdf (Year: 2015).*

(Continued)

*Primary Examiner* — Jianxun Yang
(74) *Attorney, Agent, or Firm* — Wolf, Greenfield & Sacks, P.C.

(57) ABSTRACT

System and methods for determining placement of a transducer array relative to a subject's head, which may be used in treating cancer in the subject, are provided. These techniques may include constructing, based on one or more images, a representation of the subject's head that includes information for a plurality of structures including one or more tumors positioned within the subject's brain. The representation of the subject's head may be used to calculate electric field propagation for one or more arrangements of a transducer array on a surface of the subject's head. These techniques may further include determining one or more rate of energy absorption distributions and/or one or more elec- (Continued)

tric field distributions using the calculated electric field propagation for multiple arrangements of the transducer array. A rate of energy absorption distribution may indicate a rate of energy absorbed at the one or more tumors. An electric field distribution may indicate an amount of electric field at individual regions of the subject's brain that include the one or more tumors and span across the entirety of the subject's brain. Using the one or more rate of energy absorption distributions and/or the one or more electric field distributions, an indication of how to place the transducer array on the subject's head such that at least a portion of the one or more tumors are exposed to electric fields emitted by the transducer array may be generated.

31 Claims, 17 Drawing Sheets

(51) Int. Cl.
 *G16H 50/50* (2018.01)
 *G16H 40/63* (2018.01)
 *A61N 1/04* (2006.01)
 *A61N 1/08* (2006.01)
(52) U.S. Cl.
 CPC ............... *A61N 1/08* (2013.01); *G16H 20/40* (2018.01); *G16H 40/63* (2018.01); *G16H 50/50* (2018.01)
(58) Field of Classification Search
 CPC ...... A61N 1/40; A61N 1/36025; G16H 20/40; G16H 50/50; G16H 40/63
 See application file for complete search history.

(56) References Cited

U.S. PATENT DOCUMENTS

| | | | |
|---|---|---|---|
| 2012/0226200 A1* | 9/2012 | Wagner | A61H 23/0236 601/2 |
| 2016/0055304 A1* | 2/2016 | Russell | A61N 1/36034 705/3 |

OTHER PUBLICATIONS

International Search Report and Written Opinion for International Application No. PCT/US2017/053051 dated Aug. 20, 2018.
International Preliminary Report on Patentability for International Application No. PCT/US2017/053051 dated Apr. 4, 2019.
[No Author Listed], Food and Drug Administration Neurological Devices Panel. NovoCure Ltd. NovoTTF-100A System. Mar. 17, 2011. 263 pages. https://web.archive.org/web/20170221214539/Http://Www.Fda.Gov/Ucm/Groups/Fdagov-Public/@Fdagov-Afda-Adcom/Documents/Document/Ucm247168.Pdf [last accessed Jun. 17, 2019 using Internet Archive Wayback Machine].
Gera et al., Tumor treating fields perturb the localization of septins and cause aberrant mitotic exit. PLoS One. May 26, 2015;10(5):e0125269. doi: 10.1371/journal.pone.0125269.
Gur et al., Gender differences in age effect on brain atrophy measured by magnetic resonance imaging. Proc Natl Acad Sci U S A. Apr. 1, 1991;88(7):2845-9.
Hasgall et al., IT'IS Database for thermal and electromagnetic parameters of biological tissues. Version 4.0. May 15, 2018. doi: 10.13099/VIP21000-04-0. itis.swiss/database. https://itis.swiss/virtual-population/tissue-properties/overview [last accessed on Jun. 17, 2019].
Hoelscher et al., SELDI-TOF analysis of glioblastoma cyst fluid is an approach for assessing cellular protein expression. Neurol Res. Dec. 2013;35(10):993-1001. doi:10.1179/016164113X13756993777580.
Kirson et al., Alternating electric fields arrest cell proliferation in animal tumor models and human brain tumors. Proceedings of the National Academy of Sciences of the United States of America. 2007;104(24):10152-10157.
Kirson et al., Disruption of cancer cell replication by alternating electric fields. Cancer Res. May 1, 2004;64(9):3288-95.
Lohle et al., Analysis of fluid in cysts accompanying various primary and metastatic brain tumours: proteins, lactate and pH. Acta Neurochir (Wien). 1998;140(1):14-9.
Lok et al., Tumor treating fields therapy device for glioblastoma: physics and clinical practice considerations. Expert Rev Med Devices. 2015;12(6):717-26. doi: 10.1586/17434440.2015.1086641.
Miranda et al., Predicting the electric field distribution in the brain for the treatment of glioblastoma. Phys Med Biol. Aug. 7, 2014;59(15):4137-47. doi: 10.1088/0031-9155/59/15/4137.
Stupp et al., Maintenance Therapy With Tumor-Treating Fields Plus Temozolomide vs Temozolomide Alone for Glioblastoma: A Randomized Clinical Trial. JAMA. Dec. 15, 2015;314(23):2535-43. doi: 10.1001/jama.2015.16669.
Stupp et al., NovoTTF-100A versus physician's choice chemotherapy in recurrent glioblastoma: a randomized phase III trial of a novel treatment modality. Eur J Cancer. Sep. 2012;48(14):2192-202. doi: 10.1016/j.ejca.2012.04.011.
Wenger et al., Improving Tumor Treating Fields Treatment Efficacy in Patients With Glioblastoma Using Personalized Array Layouts. Int J Radiat Oncol Biol Phys. Apr. 1, 2016;94(5):1137-43. doi:10.1016/j.ijrobp.2015.11.042.
Wenger et al., The electric field distribution in the brain during TTFields therapy and its dependence on tissue dielectric properties and anatomy: a computational study. Phys Med Biol. Sep. 21, 2015;60(18):7339-57. doi: 10.1088/0031-9155/60/18/7339.
Wong, Tumor growth, invasion, and angiogenesis in malignant gliomas. J Neurooncol. May 2006;77(3):295-6. doi: 10.1007/s11060-005-9042-8.
E. Lok et al., "Computed modeling of alternating electric fields therapy for recurrent glioblastoma," *Cancer Medicine* 2015, 4(11); 1697-99.

\* cited by examiner

EVH and SARVH of GTV

| Case | E_AUC | VE150 | E95% | E50% | E20% | SAR_AUC | VSAR7.5 | SAR95% | SAR50% | SAR20% |
|---|---|---|---|---|---|---|---|---|---|---|
| Original Tumor | 104.0 | 21.7% | 57.2 | 89.9 | 153.6 | 5.9 | 13.9% | 2.1 | 4.1 | 6.2 |
| Icosahedron | 101.1 | 17.9% | 64.5 | 92.1 | 144.2 | 5.0 | 8.7% | 2.3 | 4.3 | 5.8 |
| Cube | 101.1 | 18.5% | 62.8 | 90.8 | 146.1 | 5.0 | 8.7% | 2.3 | 4.2 | 5.9 |
| Cylinder | 99.5 | 15.8% | 63.0 | 91.2 | 135.0 | 5.1 | 8.3% | 2.3 | 4.2 | 5.7 |
| Sphere | 96.7 | 13.7% | 63.7 | 92.3 | 115.0 | 4.8 | 7.0% | 2.3 | 4.3 | 5.4 |
| Cone Anterior | 122.0 | 42.6% | 71.1 | 109.2 | 163.9 | 6.5 | 25.3% | 2.8 | 5.3 | 7.8 |
| Cone Posterior | 113.9 | 32.8% | 66.7 | 98.6 | 160.3 | 5.5 | 11.2% | 2.6 | 5.0 | 6.7 |
| Cone Left | 99.4 | 19.3% | 55.8 | 86.3 | 147.6 | 5.5 | 12.5% | 2.0 | 3.9 | 5.9 |
| Cone Right | 104.3 | 23.4% | 61.3 | 89.5 | 155.1 | 5.3 | 10.6% | 2.3 | 4.2 | 6.3 |
| Cone Superior | 77.9 | 0.4% | 51.0 | 82.7 | 94.9 | 3.5 | 3.4% | 0.9 | 3.2 | 5.2 |
| Cone Inferior | 117.1 | 38.9% | 66.1 | 96.2 | 162.7 | 5.7 | 12.9% | 2.6 | 4.9 | 7.1 |

FIG. 11C

SYSTEM AND METHODS FOR CANCER TREATMENT USING ALTERNATING ELECTRIC FIELDS

RELATED APPLICATIONS

The present application is a national stage filing under 35 U.S.C. § 371 of international PCT application, PCT/US2017/053501, filed Sep. 22, 2017, which claims the benefit under 35 U.S.C. § 119(e) of U.S. Provisional Patent Application Ser. No. 62/399,301 titled "SYSTEM AND METHODS FOR CANCER TREATMENT USING ALTERNATING ELECTRIC FIELDS," filed Sep. 23, 2016, the entire contents of each of which is incorporated herein by reference in its entirety.

BACKGROUND

Field

The present application relates to techniques for operating one or more transducer arrays to apply an alternating electric field to treat cancer in a patient.

Related Art

Low-intensity alternating electric fields can be used to treat cancer, including glioblastoma tumors within a patient's brain. This type of electromagnetic field therapy may be called tumor treating fields (TTF or TTFields), which can be tuned to a frequency between 100 kHz to 300 kHz. The alternating electric fields may disrupt cell division in cancer cells by inhibiting or reducing formation of intracellular protein structures, such as microtubules, where the subunit proteins (e.g., tubulin, septin) have large dipole moments to be influenced by the alternating electric fields. In the presence of the alternating electric fields, such intracellular protein structures may not properly form leading to improper cell division or cell death.

BRIEF SUMMARY

According to an aspect of the present application, an apparatus is provided. The apparatus includes circuitry configured to construct, based on at least one image, a representation of a subject's head that includes information for a plurality of structures including at least one tumor positioned within the subject's brain. The circuitry is further configured to determine, by using the representation of the subject's head to calculate electric field propagation for a plurality of arrangements of at least one transducer on a surface of the subject's head, at least one rate of energy absorption distribution for the plurality of arrangements. The at least one rate of energy absorption distribution indicates a rate of energy absorbed at the at least one tumor. The circuitry is further configured to generate, based on the at least one rate of energy absorption distribution, an indication of how to place at least one transducer to expose at least a portion of the at least one tumor to electric fields emitted by the at least one transducer. The apparatus further includes a user interface configured to present, to a user, the indication of how to place the at least one transducer relative to the subject's head.

In some embodiments, the representation of the subject's head includes at least one structure proximate to the at least one tumor. In some embodiments, the at least one structure includes an intracranial structure. In some embodiments, the at least one structure includes an artificial structure introduced into the subject's head. In some embodiments, the artificial structure includes an implantable electrode configured to emit an electric field.

In some embodiments, the representation of the subject's head and/or other anatomical structures includes positional information for the plurality of structures. In some embodiments, the representation of the subject's head includes at least one material property value for the plurality of structures. In some embodiments, the at least one material property includes electric conductivity, relative permittivity, thermal conductivity, heat capacity, physical density, and/or Young's modulus. In some embodiments, the at least one material property includes at least one anisotropic dielectric property. In some embodiments, the at least one material property includes at least one isotropic dielectric property. In some embodiments, the circuitry is further configured to receive at least one image obtained by diffusion tensor imaging and determine the at least one anisotropic dielectric property based on the at least one image obtained by diffusion tensor imaging. In some embodiments, the circuitry is further configured to receive at least one image obtained by magnetic resonance imaging, computed tomography, and/or positron emission tomography. In some embodiments, the circuitry is further configured to generate a three-dimensional volumetric representation of subject's anatomy.

In some embodiments, determining the at least one rate of energy absorption distribution further comprises determining a rate of energy absorption at a location corresponding to the at least one tumor. In some embodiments, determining the at least one rate of energy absorption distribution includes determining a specific absorption rate distribution for each of the plurality of arrangements. In some embodiments, individual arrangements of the plurality of arrangements have different positions of the at least one transducer on the subject's head.

In some embodiments, the plurality of structures includes a necrotic core within the tumor. In some embodiments, the plurality of structures includes a resection cavity. In some embodiments, the information for the plurality of structures includes a thickness of cerebrospinal fluid. In some embodiments, the information for the plurality of structures includes a volume of at least one of the plurality of structures. In some embodiments, the information for the plurality of structures includes a volume for at least one of scalp, white matter, grey matter, brain matter, and cerebrospinal fluid.

In some embodiments, constructing the representation of the subject's head includes identifying volumes for individual structures using the at least one image. In some embodiments, identifying volumes for individual structures includes segregating the at least one image into regions that correspond to individual structures of the plurality of structures and determining volumes associated with the regions. In some embodiments, determining the at least one rate of energy absorption distribution includes determining a rate of energy absorption distribution for individual structures of the plurality of structures. In some embodiments, generating the indication further comprises determining, for at least one of the plurality of arrangements, an amount of energy absorption for individual structures of the plurality of structures based on the at least one rate of energy absorption distribution.

In some embodiments, generating the indication further comprises identifying at least one arrangement from among the plurality of arrangements as having the highest amount of energy absorption at the at least one tumor. In some embodiments, generating the indication further comprises: determining, for a first arrangement of the plurality of arrangements, a first amount of energy absorption at the at least one tumor; determining, for a second arrangement of the plurality of arrangements, a second amount of energy absorption at the at least one tumor; and identifying the first arrangement or the second arrangement as the indication of how to place at least one transducer based on comparing the first amount of energy absorption to the second amount of energy absorption.

According to an aspect of the present application, a system is provided. The system may include at least one transducer configured to emit an alternating electric field. The system may further include circuitry configured to construct, based on at least one image, a representation of a subject's head that includes information for a plurality of structures including at least one tumor positioned within the subject's brain. The circuitry is further configured to determine, by using the representation of the subject's head to calculate electric field propagation for a plurality of arrangements of at least one transducer on a surface of the subject's head, at least one rate of energy absorption distribution for the plurality of arrangements. The at least one rate of energy absorption distribution indicates a rate of energy absorbed at the at least one tumor. The circuitry is further configured to generate, based on the at least one rate of energy absorption distribution, an indication of how to place the at least one transducer to expose at least a portion of the at least one tumor to electric fields emitted by the at least one transducer. The system further includes a user interface configured to present, to a user, the indication of how to place the at least one transducer. In some embodiments, the rate of energy absorption distribution for the plurality of arrangements includes at least one specific absorption rate distribution for the plurality of arrangements.

According to an aspect of the present application, a method is provided. The method includes constructing, based on at least one image, a representation of a subject's head that includes information for a plurality of structures including at least one tumor positioned within the subject's brain. The method further includes determining, by using the representation of the subject's head to calculate electric field propagation for a plurality of arrangements of at least one transducer on a surface of the subject's head, at least one rate of energy absorption distribution for the plurality of arrangements. The at least one rate of energy absorption distribution indicates a rate of energy absorbed at the at least one tumor. The method further includes generating, based on the at least one rate of energy absorption distribution, an indication of how to place at least one transducer array to expose at least a portion of the tumor to electric fields emitted by the at least one transducer array.

According to an aspect of the present application, an apparatus is provided. The apparatus includes circuitry configured to construct, based on at least one image, a representation of a subject's head that includes information for a plurality of structures including at least one tumor positioned within the subject's brain. The circuitry is further configured to determine, by using the representation of the subject's head to calculate electric field propagation for a plurality of arrangements of at least one transducer on a surface of the subject's head, at least one electric field distribution within the subject's brain for the plurality of arrangements. The at least one electric field distribution indicates an amount of electric field at individual regions of the subject's brain that include the at least one tumor and span across the entirety of the subject's brain. The circuitry is further configured to generate, based on the at least one electric field distribution, an indication of how to place at least one transducer to expose at least a portion of the at least one tumor to electric fields emitted by the at least one transducer. The apparatus further comprises a user interface configured to present, to a user, the indication of how to place the at least one transducer relative to the subject's head.

In some embodiments, determining the at least one electric field distribution further comprises determining at least one electric field distribution for the plurality of arrangements. The at least one electric field distribution indicates an amount of electric field at the at least one tumor. In some embodiments, determining the at least one electric field distribution further comprises determining a level of electric field intensity at a location corresponding to the at least one tumor. In some embodiments, determining the at least one electric field distribution further comprises determining an electric field at a location corresponding to the at least one tumor. In some embodiments, the at least one electric field distribution indicates an amount of electric field at individual regions of the subject's brain that include the at least one tumor and span across the entirety of the subject's brain.

In some embodiments, the representation of the subject's head includes at least one structure proximate to the at least one tumor. In some embodiments, the at least one structure includes an intracranial structure. In some embodiments, the at least one structure includes an artificial structure introduced into the subject's head. In some embodiments, the artificial structure includes an implantable electrode configured to emit an electric field.

In some embodiments, the representation of the subject's head includes positional information for the plurality of structures. In some embodiments, the representation of the subject's head includes at least one material property value for the plurality of structures. In some embodiments, the at least one material property includes electric conductivity, relative permittivity, thermal conductivity, heat capacity, physical density, and/or Young's modulus. In some embodiments, the at least one material property includes at least one isotropic dielectric property and/or at least one anisotropic dielectric property.

In some embodiments, the circuitry is further configured to receive at least one image obtained by diffusion tensor imaging and determine the at least one anisotropic dielectric property based on the at least one image obtained by diffusion tensor imaging. In some embodiments, determining the at least one electric field distribution includes determining an electric field distribution for each of the plurality of arrangements. In some embodiments, individual arrangements of the plurality of arrangements have different positions of the at least one transducer on the subject's head. In some embodiments, the plurality of structures includes a necrotic core within the at least one tumor. In some embodiments, the plurality of structures includes a resection cavity. In some embodiments, the information for the plurality of structures includes a thickness of cerebrospinal fluid. In some embodiments, the information for the plurality of structures includes a volume of at least one of the plurality of structures. In some embodiments, the information for the plurality of structures includes a volume for at least one of scalp, white matter, grey matter, brain matter, and cerebrospinal fluid.

In some embodiments, constructing the representation of the subject's head includes identifying volumes for individual structures using the at least one image. In some embodiments, identifying volumes for individual structures includes segregating the at least one image into regions that correspond to individual structures of the plurality of structures and determining volumes associated with the regions. In some embodiments, determining the at least one electric field distribution includes determining an electric field distribution for individual structures of the plurality of structures.

In some embodiments, generating the indication further comprises determining, for at least one of the plurality of arrangements, an amount of electric field for individual structures of the plurality of structures based on the at least one electric field distribution. In some embodiments, generating the indication further comprises identifying at least one arrangement from among the plurality of arrangements as having the highest amount of electric field intensity at the at least one tumor. In some embodiments, generating the indication further comprises: determining, for a first arrangement of the plurality of arrangements, a first amount of electric field intensity at the at least one tumor; determining, for a second arrangement of the plurality of arrangements, a second amount of electric field intensity at the at least one tumor; and identifying the first arrangement or the second arrangement as the indication of how to place at least one transducer based on comparing the first amount of electric field intensity to the second amount of electric field intensity.

According to an aspect of the present application, a system is provided. The system includes at least one transducer configured to emit an alternating electric field. The system further includes circuitry configured to construct, based on at least one image, a representation of a subject's head that includes information for a plurality of structures including at least one tumor positioned within the subject's brain. The circuitry is further configured to determine, by using the representation of the subject's head to calculate electric field propagation for a plurality of arrangements of at least one transducer on a surface of the subject's head, at least one electric field distribution within the subject's brain for the plurality of arrangements. The at least one electric field distribution indicates an amount of electric field at individual regions of the subject's brain that include the at least one tumor and span across the entirety of the subject's brain. The circuitry is further configured to generate, based on the at least one electric field distribution, an indication of how to place at least one transducer to expose at least a portion of the at least one tumor to electric fields emitted by the at least one transducer. The system further includes a user interface configured to present, to a user, the indication of how to place the at least one transducer relative to the subject's head.

According to an aspect of the present application, a method is provided. The method includes constructing, based on at least one image, a representation of a subject's head that includes information for a plurality of structures including at least one tumor positioned within the subject's brain. The method further includes determining, by using the representation of the subject's head to calculate electric field propagation for a plurality of arrangements of at least one transducer on a surface of the subject's head, at least one electric field distribution within the subject's brain for the plurality of arrangements. The at least one electric field distribution indicates an amount of electric field at individual regions of the subject's brain that include the at least one tumor and span across the entirety of the subject's brain. The method further includes generating, based on the at least one electric field distribution, an indication of how to place at least one transducer to expose at least a portion of the at least one tumor to electric fields emitted by the at least one transducer.

According to an aspect of the present application, a method is provided. The method includes constructing, based on at least one image, a representation of a subject's head and/or other anatomical structures that includes information for a plurality of structures including a tumor positioned within the subject's brain and/or other anatomical sites and determining, by using the representation of the subject's head and/or other anatomical sites to calculate electric field propagation for a plurality of arrangements of at least one transducer on a surface of the subject's head and/or other anatomical sites, at least one electric field distribution for the plurality of arrangements. The at least one electric field distribution indicates an amount of electric field at the tumor. The method further includes generating, based on the at least one electric field distribution, an indication of how to place at least one transducer to expose at least a portion of the tumor to electric fields emitted by the at least one transducer.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 5E shows a first array placement position, which may be considered as a default array primary position. FIGS. 5A, 5B, 5C, 5D, 5F, 5G, 5H, and 5I each show different array placement positions. In FIGS. 5A, 5D, and 5G, the disks in each array are rotated in aggregate by 2-cm deviation from the primary position (FIG. 5E) in a clockwise fashion. In FIGS. 5C, 5F, and 5I, the disks in each array are rotated in aggregate by 2-cm deviation from the primary position (FIG. 5E) in a counter clockwise fashion. In FIGS. 5A, 5B, and 5C, the posterior arrays were rotated in aggregate by 2-cm deviation forward from the primary position (FIG. 5E) and the anterior arrays were moved in aggregate by 2-cm deviation forward. In FIGS. 5G, 5H, and 5I, the anterior arrays were moved in aggregate by 2-cm deviation backward from the primary position (FIG. 5E).

FIG. 5A: CW+Forward, FIG. 5B: Forward Only, FIG. 5C: CCW+Forward, FIG. 5D: CW+No AP PA Difference, FIG. 5E: Primary Position, FIG. 5F: CCW+No AP PA Difference, FIG. 5G: CW+Backward, FIG. 5H: AP Only Backward, and FIG. 5I: CCW+AP Backward. AP, antero-posterior; PA, postero-anterior; CW, clockwise; CCW, counter clockwise; EVH, electric field-volume histogram; SARVH, specific absorption rate-volume histogram; GTV, gross tumor volume; V/m, volt per meter; W/kg, watt per kilogram; SAR, specific absorption rate; $SAR_{50\%}$, the magnitude of SAR encompassing 50% of volume.

FIGS. 11A-11C show electric field and specific absorption rate quantities in the GTV geometric analysis. FIG. 11A EVH was constructed according to the geometries displayed in FIGS. 10A and 10B (A). SARVH was constructed according to the geometries displayed in FIGS. 10A and 10B. Electric field and SAR quantities are listed for various GTV geometries (C). GTV, gross tumor volume; EVH, electric field-volume histogram; SARVH, specific absorption rate-volume histogram; $E_{AUC}$, electric field area under the curve; $V_{E150}$, volume covered with electric field intensity of 150 volts per meter; $E_{95\%}$, the electric field intensity encompassing 95% of volume; $E_{50\%}$, the electric field intensity encompassing 50% of volume; $E_{20\%}$, the electric field intensity encompassing 50% of volume; SAR, specific absorption rate; $SAR_{AUC}$, SAR area under the curve; $V_{SAR7.5}$, volume covered with specific absorption rate of 7.5 watts per kilogram; $SAR_{95\%}$, the magnitude of specific absorption rate encompassing 95% of volume; $SAR_{50\%}$, the magnitude of specific absorption rate encompassing 50% of volume; $SAR_{20\%}$, the magnitude of specific absorption rate encompassing 20% of volume.

DETAILED DESCRIPTION

Figure 1:
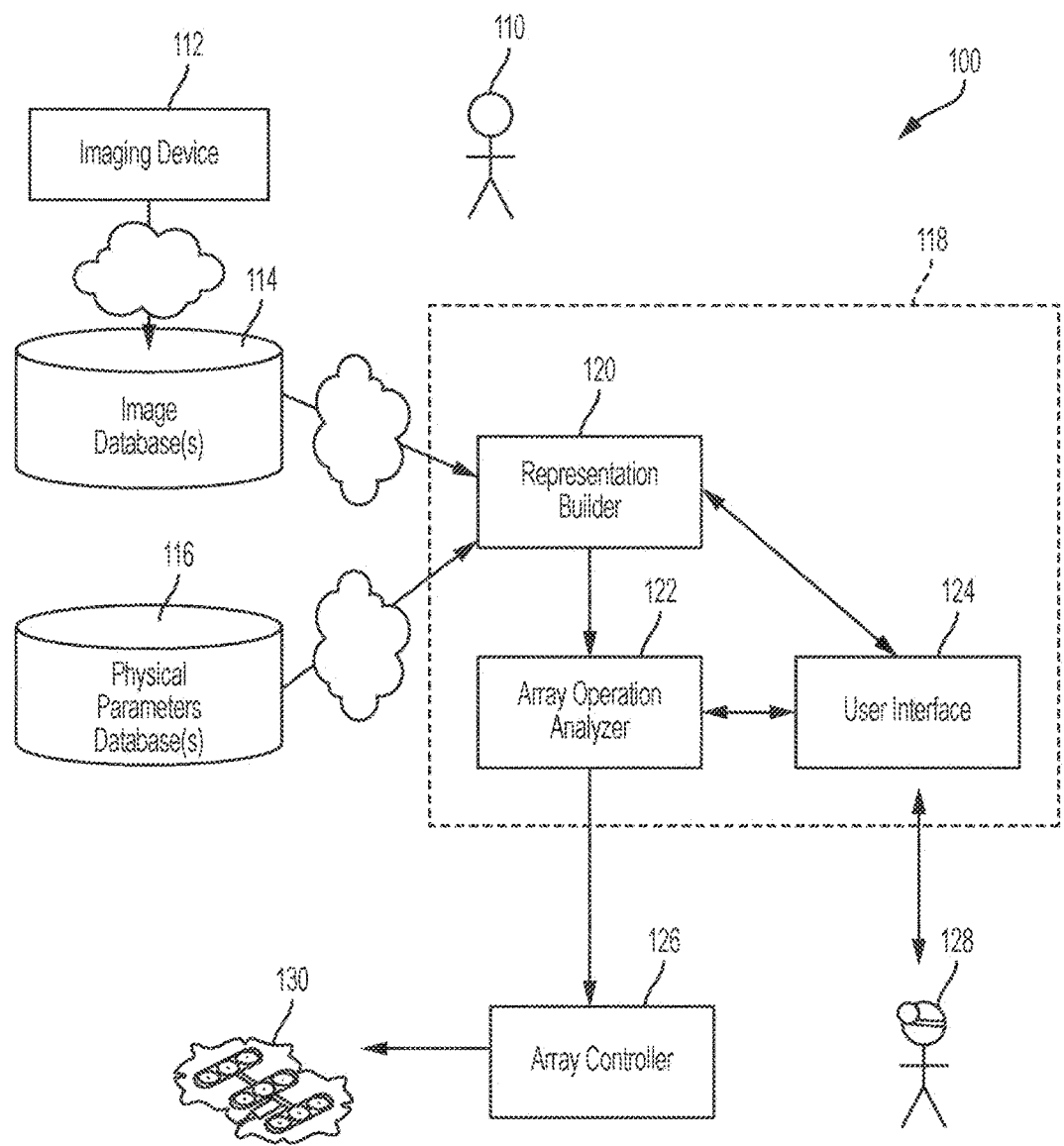
FIG. 1 is a schematic of an exemplary system for determining parameters of one or more transducer arrays used to treat cancer cells, according to some embodiments.

Aspects of the present application relate to techniques for determining parameters of one or more transducer arrays used to treat cancer cells (e.g., glioblastoma cells in a patient's brain). In some embodiments, one or more transducer arrays may be used to treat a tumor in a subject, such as the head of the subject and/or other anatomical sites. The one or more transducers may be placed on a surface of the subject proximate to the location of the tumor and may emit alternating electric fields. In embodiments where the one or more transducer arrays are used to treat a brain tumor, the one or more transducer arrays may be placed on the subject's head (e.g., on the subject's scalp). Although techniques of the present application are described using examples of treating a tumor located in a subject's head, these examples are non-limiting. It should be appreciated that the techniques described herein may be used to treat tumors and/or cancer cells positioned in other anatomical sites of a subject (e.g., stomach, breast, colon, lung).

Material properties (e.g., electric conductivity, relative permittivity, thermal conductivity, heat capacity, physical density, Young's modulus) of the tissue can impact propagation of electric fields within a region of the subject (e.g., head). Variation in one or more material properties of the region of the subject may distort electric field propagation, which may impact the amount of electric field the tumor in the region of the subject receives and the effectiveness in the treatment. Material properties of the tissue may also impact the rate of energy absorption (e.g., specific absorption rate) by different regions of the tissue while electric fields propagate through the subject. In embodiments where the one or more transducer arrays are used to treat brain cancer, intracranial structures (e.g., necrotic core, resection cavity, white matter, grey matter, brain matter) and/or extracranial structures (e.g., an implantable electrode, modulator) may be considered. Intracranial and/or extracranial structures can vary in position and/or geometry for different individuals. Characteristics of a tumor including, location, size, shape, geometry, and one or more material properties may vary depending on the type and/or stage of the cancer. Variation in such intracranial and/or extracranial structural features can also impact the amount of electric field the tumor receives, the rate of energy absorption, and/or effectiveness in the treatment. By gaining an understanding of how electric field propagation within a subject's head, or another anatomical site, depends on variation in material properties, position, and/or geometry of the intracranial structures, electric field treatment of tumors can be improved.

Applicants have appreciated that a representation of a region of a subject that includes information about different structures can be used as a model to calculate electric field propagation. In embodiments where the region of the subject is the subject's head, intracranial and/or extracranial structures can be used in a model to calculate electric field propagation, and material properties of those structures may be used to determine electric field propagation for a particular arrangement of electrodes positioned on the subject's head. The representation of the subject's head may be constructed based on one or more images, such as images of the subject's head that provide information for different intracranial structures (e.g., tumor, necrotic core, cerebellum) and/or extracranial structures (e.g., scalp). In some embodiments, constructing a representation of the subject's head may include identifying volumes for individual structures, such by using the images to estimate volumes for structures included in the images. A volume for a structure may be identified by outlining a three-dimensional shape of a structure included in one or more images and extrapolating a volume for the structure based on the outlined shape. Volumes for multiple structures may be identified by segregating one or more images into regions that correspond to individual structures and determining volumes associated with the regions. In this manner, electric field propagation within different intracranial structures and/or extracranial structures, including the amount of electric field and rate of energy absorption for different structures, may be identified.

Calculating electric field propagation may include modeling placement of one or more transducer arrays with respect to the representation of the region of the subject and determining distribution of the electric field and/or rate of energy absorption for that particular placement of the one or more transducer arrays. The distribution of the electric field may provide an indication of an amount of electric field the region of the subject may receive if that particular arrangement of the one or more transducer arrays was used on the subject. The distribution of rate of energy absorption may provide an indication of a rate of energy absorption (e.g., specific absorption rate) for a region of the subject for a particular arrangement of the one or more transducer arrays. In some embodiments, a region of interest within a subject may be a tumor positioned with the subject's head, and the distribution of the electric field may provide an indication of the amount of electric field received by the tumor. Similarly, the distribution of rate of energy absorption may provide an indication of a rate of energy absorption for the tumor.

Electric field distributions and/or rate of energy absorption distributions for different placements of the one or more transducer arrays can be obtained with the representation of the region of the subject's head and may provide an indication of how to place the one or more transducer arrays on the subject's head as part of the treatment. For different arrangements of one or more transducer arrays, distributions of electric field and/or rate of energy absorption can be determined and used to evaluate the different arrangements. Different transducer arrangements may be evaluated based on one or more characteristics (e.g., amount of electric field, rate of energy absorption, amount of energy absorbed) at a tumor location determined from the distributions of electric field and/or rate of energy absorption. By comparing different distributions for different transducer arrangements, a particular transducer arrangement may be selected from among the different transducer arrangements as providing a particular amount of energy absorption and/or electric field to the tumor. In some embodiments, identifying a transducer arrangement may include selecting a transducer arrangement from among multiple different transducer arrangements as having the highest amount of energy absorption and/or highest amount of electric field at the tumor. Such a process may allow for identification of a transducer arrangement that allows for targeted and personalized delivery of electric fields and/or electric energy to the tumor, which can be used in treatment.

In addition, modeling electric field propagation for a particular transducer arrangement may allow for identification of one or more parameters (e.g., electric field magnitude, frequency, duration) used to operate one or more transducers in order to provide a particular amount of electric field and/or rate of energy absorption at a particular region, such as a tumor inside a person's head. For example, modeling how electric field propagation varies over a range of frequencies of electric fields emitted by one or more transducers may allow for identification of one or more frequencies that provide a particular amount of electric field and/or rate of energy absorption to a tumor. During operation, the one or more transducers may be controlled to emit an alternating electric field having one of the identified frequencies. As another example, modeling how electric field propagation varies over a range of electric field magnitude The aspects and embodiments described above, as well as additional aspects and embodiments, are described further below. These aspects and/or embodiments may be used individually, all together, or in any combination of two or more, as the application is not limited in this respect.

FIG. 1 illustrates an exemplary embodiment of system 100 for determining parameters of one or more transducer arrays used to treat cancer cells. System 100 includes imaging device 112, assessment system 118, and array controller 126. Imaging device 112 is configured to obtain one or more images of subject 110 that include information about intracranial and/or extracranial structures of the subject's head and/or other anatomical sites. Any suitable imaging device 112 may be used that allows for structural information of the subject's brain to be obtained. Imaging device 112 may be a magnetic resonance imaging (MRI) system (e.g., a diffusion tensor imaging MRI system, anatomic MRI system), a computed tomography (CT) system, and/or positron emission tomography (PET) system. System 100 includes one or more image databases 114, which may be accessible by imaging device 112 and/or assessment system 118. Imaging device 112 may transmit one or more images of subject 110 to image database(s) 114, which may store the one or more images. In embodiments, where imaging device 112 is a diffusion tensor imaging MRI system, one or more images obtained from the diffusion tensor imaging MRI system may provide an indication of one or more anisotropic and/or isotropic values of material properties for tissue within the anatomical site being examined, such as the subject's brain. Different anisotropic values may correspond to different regions of anatomical site. The one or more images obtained by imaging device 112 may provide an indication of a volume representative of the anatomical site and individual voxels that make up the volume may have values corresponding to different anisotropic and/or isotropic properties. In embodiments where the anatomical site is the subject's brain, variation of anisotropic and/or isotropic values within an intracranial and/or extracranial structure and/or type of tissue may be in the range of 1% to 10%, or any value or range of values within that range.

System 100 also includes one or more physical properties databases 116, which may store material property information related to one or more intracranial and/or extracranial structures and may be accessible by assessment system 118. In some embodiments, physical properties database(s) 116 may include predetermined material properties (e.g., conductivity, permittivity) for different types of intracranial and/or extracranial structures (e.g., scalp, skull, dura, cerebrospinal fluid). In some embodiments, physical properties database(s) 116 may include suitable volumes for different types of intracranial and/or extracranial structures. Table 1 provides exemplary information that may be stored in physical parameters database(s) 116. Table 1 includes volume, electric conductivity, and relative permittivity values for gross tumor volume (GTV), necrotic core, scalp, skull, dura, cerebrospinal fluid, white matter, gray matter, bilateral ventricles, brainstem, orbits, cerebellum, unspecified tissue/muscle, electrodes, and titanium wires.

TABLE 1

| Tissue Structure | Volume (cc) | Electric Conductivity σ (S/m) | Relative Permittivity $\varepsilon_r$ |
| --- | --- | --- | --- |
| GTV | 5.813874 | 2.50E−01 | 1.00E+04 |
| Necrotic Core | 2.421458 | 1.00E+02 | 1.00E+00 |
| Scalp | 524.5453 | 1.05E−03 | 1.10E+03 |
| Skull | 463.5451 | 2.11E−02 | 2.04E+02 |
| Dura | 216.8171 | 5.02E−01 | 2.90E+02 |

TABLE 1-continued

| Tissue Structure | Volume (cc) | Electric Conductivity σ (S/m) | Relative Permittivity $\varepsilon_r$ |
| --- | --- | --- | --- |
| CSF | 238.8805 | 2.00E+00 | 1.09E+02 |
| White Matter | 593.1396 | 8.68E−02 | 1.29E+03 |
| Gray Matter | 261.5665 | 1.41E−01 | 2.01E+03 |
| Bilateral Ventricle | 51.38429 | 2.00E+00 | 1.09E+02 |
| Brainstem | 28.7721 | 1.61E−01 | 2.30E+03 |
| Orbits | 12.89734 | 1.50E+00 | 9.66E+01 |
| Cerebellum | 44.55224 | 1.61E−01 | 2.30E+03 |
| Unspecified Tissue/Muscle | 133.3064 | 3.84E−01 | 6.38E+03 |
| Electrodes | N/A | 1.00E−05 | 1.10E+04 |
| Ti Wires | N/A | 1.28E+06 | 5.00E+01 |

As depicted, exemplary assessment system 118 includes representation builder 120 and array operator analyzer 122. Each of these processing components of assessment system 118 may be implemented in software, hardware, or a combination of software and hardware. Components implemented in software may comprise sets of processor-executable instructions that may be executed by the one or more processors of assessment system 118 to perform the functionality described herein. Any combination of representation builder 120 and array operator analyzer 122 may be implemented on one or more separate machines, or parts of any or all of the components may be implemented across multiple machines in a distributed fashion and/or in various combinations.

Assessment system 118 may receive one or more images of subject 110 and/or one or more physical properties and construct a representation of the subject's anatomical site (e.g., subject's brain), which may be used to determine one or more parameters used in operating one or more transducer arrays 130. Assessment system 118 may generate an indication of the one or more parameters. The indication may include how to place one or more transducers with respect to the anatomical site, for example how to position the one or more transducers relative to the subject's head. The indication may include a particular magnitude and/or frequency of the electric fields to use, and/or any other suitable type of operating parameter used to operate a transducer array 130. The indication may be presented to user 128 via user interface 124. User 128 may be a clinician, who may place one or more transducer arrays 130 onto the person's head and/or other anatomical sites. In some embodiments, assessment system 118 may transmit the indication to array controller 126, which may be any suitable computing device used to generate a control signal for one or more transducer arrays 130.

Representation builder 120 may retrieve the one or more images of subject 110 from image database(s) 114. Information for one or more intracranial structures (e.g., tumor, necrotic core) and/or extracranial structures (e.g., scalp, cerebrospinal fluid) may be determined from the one or more images. The information for the one or more intracranial and/or extracranial structures may include positions, volumes, and/or shape of one or more intracranial and/or extracranial structures. In some embodiments, values for anisotropic and/or isotropic properties of the tissue may be determined from the one or more images. Representation builder 120 may retrieve one or more physical properties from physical properties database(s) 116. Representation builder 120 may construct a representation of a subject's head, or another anatomical site, based on one or more images retrieved from image database(s) 114. The representation may be constructed in any suitable manner. In some embodiments, the representation may be constructed by segmenting different brain structures based on the one or more images. The representation of the subject's head may correspond to a volume having many voxels that form the volume. Information for a voxel may indicate one or more values corresponding to material properties of tissue corresponding to the voxel. In this manner, variation in material properties within a patient's head can be represented by the multiple voxels. In some embodiments, the representation of the subject's head can be presented on a display to user 128. In some embodiments, assessment system 118 may receive input from user 128 that can be used as input in constructing a representation by representation builder 120.

Figure 5:
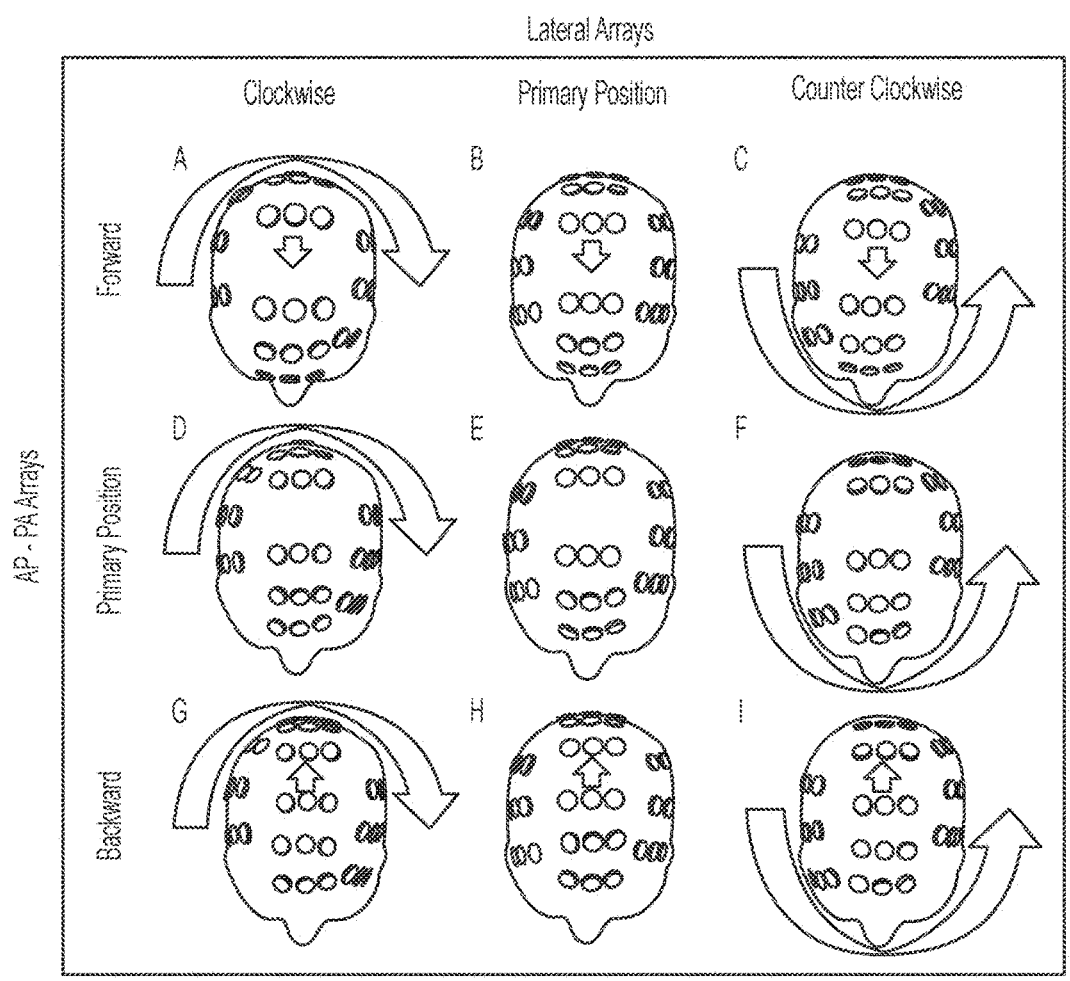
FIGS. 5A-5I show different array displacements.

Array operation analyzer 122 may receive information indicative of the representation constructed by representation builder 120 and use the information to determine one or more parameters used for operation of one or more transducer arrays 130. Array operation analyzer 122 may calculate electric field propagation within the subject's brain using one or more input parameters and determine an electric field distribution and/or rate of energy absorption (e.g., specific absorption rate) distribution. The electric field distribution may provide an indication of an amount of electric field at different locations within the anatomical site, including at a tumor. In some embodiments, the electric field distribution may include a level of electric field intensity at a location corresponding to the tumor. The rate of energy absorption distribution may provide an indication of an amount of energy deposited at different locations within the anatomical site, including at a tumor. In some embodiments, the one or more input parameters may include information identifying an arrangement of one or more transducer arrays relative to the subject's head and the electric field and/or specific absorption rate distribution generated by array operation analyzer may correspond to that particular arrangement of one or more transducer arrays. FIG. 5 shows examples of different arrangements for placing four transducer arrays on a surface of a person's head.

In some embodiments, array operation analyzer 122 may generate different electric field distributions and/or rate of energy absorption distributions for multiple arrangements of one or more transducer arrays. The different electric field and/or rate of energy absorption distributions may be assessed to identify an arrangement that provides a desired amount of electric field and/or energy absorption rate to a tumor or a region of a tumor. In some embodiments, an electric field distribution may provide an indication of tumor volume that receives the electric fields and/or the intensity of the electric field at a location corresponding to the tumor. In some embodiments, a rate of energy absorption distribution may provide an indication of tumor volume that receives the rate at which the energy deposited and/or the intensity of the energy deposited at a location corresponding to the tumor. FIGS. 6A-6D show plots of normalized volume versus electric field or specific absorption rate at a tumor for different arrangements of transducer arrays. A particular arrangement may be selected based on the amount of electric field at the tumor provided by that arrangement, such as whether the amount of electric field is above or below a threshold value and/or whether a specific absorption rate is above or below a threshold value. In some embodiments, identifying a particular arrangement may include integrating the plots of normalized volume versus electric field or specific absorption rate to identify an area under the plots, and the arrangement having the largest area may be selected. Additionally or alternatively, one or more arrangements may be selected based on whether the area under the plots for electric field and/or specific absorption rate is above a threshold amount. Array operation analyzer 122 may transmit an indication of the selected arrangement to user interface 124, which may present information identifying how to place one or more transducer arrays on the subject's head and/or other anatomical sites. In some embodiments, array operation analyzer 122 may transmit an indication of the selected arrangement to array controller 126, which is configured to operate transducer array 130.

Array operation analyzer 122 may determine an electric field and/or rate of energy absorption (e.g., specific absorption rate) distribution using any suitable computational techniques, including one or more suitable finite element solving methods. Some computational techniques may include an iterative process to reduce error for each voxel in the representation of the subject's head and/or other anatomical sites. In some embodiments, array operation analyzer 122 may implement a Newton-Raphson method and/or other numerical methods to determine an electric field distribution. Array operation analyzer 122 may determine initial and boundary conditions and input these conditions into the computational processing method used to determine an electric field and/or rate of energy absorption (e.g., specific absorption rate) distribution.

Figure 2:
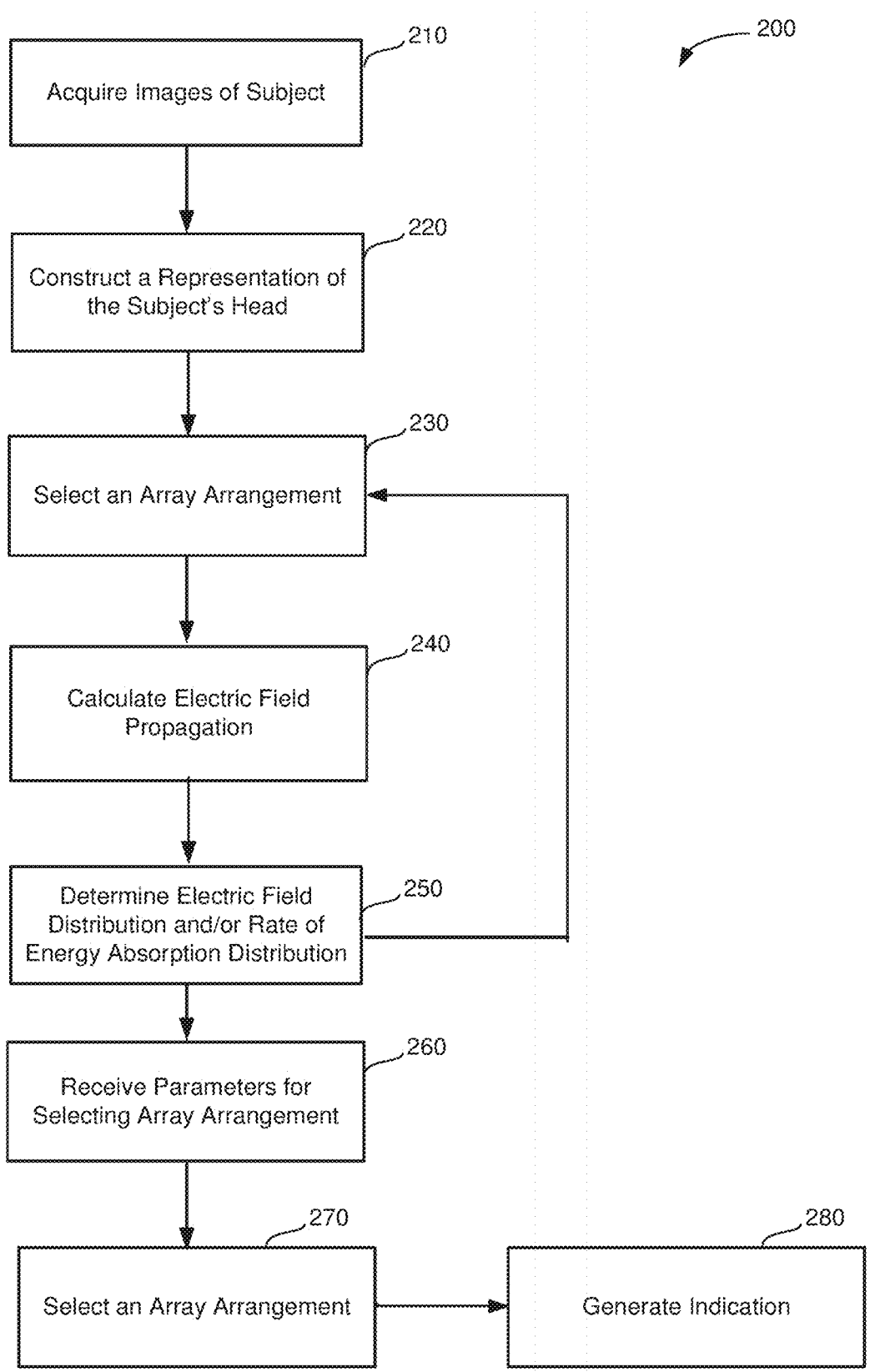
FIG. 2 is a flowchart of an exemplary method for determining parameters of one or more transducer arrays used to treat cancer cells, according to some embodiments.

FIG. 2 depicts an exemplary method for determining parameters of one or more transducer arrays used to treat cancer cells using the techniques described herein, including the system described in FIG. 1. Method 200 begins at step 210 where one or more images of a subject are acquired, such as by imaging device 112. In some embodiments, an imaging device configured to perform diffusion tensor imaging may be used to obtain one or more images of a subject.

The one or more images of the subject may be used to construct a representation of the subject's head and/or other anatomical sites, such as by representation builder 120, by step 220 of method 200. The representation may then be used to determine electric field propagation based on different transducer array arrangements. The representation may be of the subject's head and may include information for multiple structures, such as intracranial and extracranial structures, including one or more tumors positioned within the subject's brain. In some embodiments, the representation of the subject's head may include one or more structures (e.g., intracranial structure, artificial structure) proximate to the one or more tumors. Examples of structures that may be included in a representation include a necrotic core of a tumor, resection cavity, cerebrospinal fluid, white matter, grey matter, brain matter, and scalp. An example of an artificial structure that may be included in a representation is an implantable electrode positioned within the subject's head, where the implantable electrode is configured to emit electric fields. Another example of an artificial structure that may be included in a representation is a modulator positioned between a transducer and a tumor, where the modulator is configured to direct some or all of the electric field emitted by the transductor towards the tumor. In some embodiments, the modulator may be a passive modulator. In other embodiments, the modulator may be an active modulator and configured to receive control signals that operate the modulator to control the amount and directionality of electric fields. The representation may include positional information for multiple structures. For example, the positional information may include information indicating size, shape, geometry, location, volume, thickness, and any other suitable characteristic of a structure. In some cases, the positional information may include relative positions and/or distances between different structures.

The representation may include information indicating one or more material properties associated with the one or more structures included in the representation. Examples of material properties that may be included in a representation include electric conductivity, relative permittivity, thermal conductivity, heat capacity, physical density, and Young's modulus. In some embodiments, a material property included in a representation may be an isotropic dielectric property. In some embodiments, a material property included in a representation may be an anisotropic dielectric property. In such cases, an image obtained by diffusion tensor imaging may be used to determine the anisotropic dielectric property.

In some embodiments, constructing the representation may include identifying volumes for individual structures using the one or more images. Identifying the volumes for individual structures may include segregating the one or more images into regions that correspond to individual structures and determining volumes associated with the regions. For example, a set of images of a subject's head may be segmented into regions corresponding to different structures, such as white matter, grey matter, scalp, necrotic core of a tumor, and cerebrospinal fluid, and volumes associated with those regions may be determined as estimated volumes for those structures.

At step 230 of method 200, a transducer array arrangement may be selected, such as by array operation analyzer 122. The transducer array arrangement may be selected from among multiple arrangements that each have different positions of the transducer arrays on the subject's head. Examples of possible transducer array arrangements are shown in FIG. 5.

At step 240, the transducer array arrangement selected in step 230 may be used with the representation construction in step 220 to calculate electric field propagation within a subject's head, such as by array operation analyzer 122. Electric field propagation may depend on one or more parameters of how the transducers in the array are operated, including a magnitude and/or frequency of the electric field emitted by the transducers. These parameters may be inputted by a user and/or stored in one or more databases.

An electric field distribution and/or a rate of energy absorption distribution may be determined by step 250, such as by array operation analyzer 122. The electric field distribution and/or rate of energy absorption distribution may be determined using the electric field propagation calculations determined by step 240 and/or a representation of the subject's head constructed by step 230. In embodiments where a rate of energy absorption distribution is determined, the distribution may include a rate of energy absorption at a location corresponding to one or more tumors. In some embodiments, the rate of energy absorption distribution may be a specific absorption rate distribution.

In some embodiments, determining a rate of energy absorption distribution includes determining a rate of energy absorption distribution for individual structures, which may be determined using volumes associated with the individual structures. For example, one of the segregated structures may include the cerebrospinal fluid of the subject's brain, and determining a rate of energy distribution may include determining a rate of energy distribution within a volume and/or thickness that corresponds to the cerebrospinal fluid. In some embodiments, determining an electric field distribution includes determining an electric field distribution for individual structures.

The method may continue by repeating steps 230, 240, and 250 for different transducer array arrangements until a desired number of unique arrangements have an associated electric field and/or rate of energy absorption distribution. For example, multiple distributions may be obtained by determining a rate of energy absorption distribution for each transducer arrangement in a set of transducer arrangements that have different positions of one or more transducers on the subject's head.

At step 260, parameters used to select a transducer array arrangement may be received, such as by user input via user interface 124. The parameters used to select a transducer array arrangement may include a desired amount of electric field and/or specific absorption rate at a region of a tumor.

At step 270, a transducer array arrangement may be selected. In some embodiments, selection of a transducer array arrangement may include identifying one or more transducer arrangements from among multiple arrangements as having the highest amount of energy absorption and/or electric field intensity at a tumor. For example, an amount of energy absorption and/or electric field intensity at a tumor may be determined for multiple transducer arrangements, and identifying one of the arrangements may include comparing the amount of energy absorption and/or electric field intensity at the tumor. When the amount of energy absorption and/or electric field intensity is higher for first transducer arrangement in comparison to a second transducer arrangement, then the first transducer arrangement may be selected. In other embodiments, a transducer array arrangement may be selected in accordance with the parameters received by step 260.

At step 280, an indication identifying the selected transducer array arrangement may be generated, such as by array operation analyzer 122. The indication may be transmitted to user interface 124 and/or array controller 126. The indication may include positional information identifying locations of the subject's head where one or more transducers should be placed when providing treatment. The indication may include one or more parameters (e.g., magnitude of emitted electric field, frequency of alternating electric field) that should be used when operating the one or more transducers. In embodiments that include an implantable electrode positioned within the subject's head and configured to emit electric fields, the indication may include one or more parameters used to operate the implantable electrode, including magnitude, frequency, and duration of the electric fields emitted by the implantable electrode. In embodiments that include a modulator, the indication may include information on how to position the modulator relative to the subject's head and/or the transducer array. In embodiments where the modulator is an active modulator, the indication may include information on how to operate the active modulator, including one or more parameters (e.g., magnitude, frequency, duration of electric fields) of how the active modulator directs and/or modulates electric fields emitted by the transducer array.

Additional aspects and embodiments of the present application are described further below.

Tumor Treating Fields (TTFields) therapy is an approved treatment that has known clinical efficacy against recurrent and newly diagnosed glioblastoma. However, the distribution of the electric fields and the corresponding pattern of energy deposition in the brain are poorly understood. To evaluate the physical parameters that may influence TTFields, post-acquisition MP-RAGE, T1 and T2 MRI sequences from a responder with a right parietal glioblastoma were anatomically segmented and then solved using finite element method to determine the distribution of the electric fields and rate of energy deposition at the gross tumor volume (GTV) and other intracranial structures. Electric-field volume histogram (EVH) and specific absorption rate-volume histogram (SARVH) were constructed. The electric field parameters $E_{AUC}$, $V_{E150}$, $E_{95\%}$, $E_{50\%}$, and $E_{20\%}$, as well as the SAR parameters $SAR_{AUC}$, $V_{SAR7.5}$, $SAR_{95\%}$, $SAR_{50\%}$, and $SAR_{20\%}$, facilitated comparison between models derived from various conditions. Specifically, TTFields at the GTV were influenced by the dielectric characteristics of the adjacent tissues as well as the GTV itself, particularly the presence or absence of a necrotic core. The thickness of the cerebrospinal fluid on the convexity of the brain and the geometry of the tumor were also relevant factors. Finally, tumor geometry and the position of the arrays also influenced the electric field distribution and rate of energy deposition in the GTV. Collectively, EVH and SARVH facilitate the comparison of electric field distribution and rate of energy deposition from different models. A personalized approach for TTFields treatment can be developed when various patient-related and tumor-related factors are incorporated into the planning procedure.

Tumor treating fields (TTFields) are alternating electric fields tuned to a frequency between 100 to 300 kHz that have anti-mitotic properties against rapidly dividing cancer cells. When properly applied, these fields disrupt large protein structures with large dipole moments, such as Tubulin and Septin, which are important for proper cytokinesis. TTFields may have equivalent efficacy against recurrent glioblastoma when compared to chemotherapies and, when added to maintenance temozolomide, may benefit in newly diagnosed glioblastoma patients when compared to maintenance temozolomide alone. Although the clinical efficacy against glioblastoma is apparent, the intracranial distribution of the electric fields and to what extent the fields retard tumor growth remain largely unknown.

TTFields are applied to the shaved scalp via two pairs of orthogonally positioned transducer arrays. Placement of the arrays is determined by the proprietary NovoTAL™ software that generates an array layout diagram. Each array has nine ceramic disks acting like disk sources for the electric fields. However, unlike high-energy ionizing radiation that can penetrate intracranial structure in a straight beam path, the intensity and directionality of electric fields are heavily influenced by the local dielectric properties of various structures in the head, particularly the electric conductivity and the relative permittivity of brain tissue. As the conductivity and permittivity of tissues vary, the absorption and attenuation of TTFields will change and thus the distribution of these fields will be distorted. In addition, there is no accepted conductivity and permittivity values for human tumors, as each individual tumor will vary in size, geometry, location within the brain, cellular composition, and presence or absence of necrosis, all of which can influence the aggregate dielectric properties of the human tumor(s). Therefore, to properly evaluate how tissue dielectric properties influence the applied TTFields in the glioblastoma patient, a computer simulated model, best solved by the finite element method, is needed. This model takes into account the normal brain structures, the gross tumor volume (GTV), the presence or absence of a necrotic core within the tumor, and local tissue conductivity and relative permittivity values. Finite element modeling of a patient who responded to TTFields treatment showed that there is heterogeneity in the electric field intensity and the rate of energy absorbed as shown by the electric field-volume histogram (EVH) and the specific absorption rate-volume histogram (SARVH). The intensity of the electric fields and the specific absorption rate (SAR) are also influenced by the placement of the transducer arrays, the presence or absence of a necrotic core within the glioblastoma, the thickness of the cerebrospinal fluid on the convexity of the brain, and tumor geometry.

Exemplary Materials and Methods

Post-acquisition MP-RAGE, T1 and T2 MRI sequences from a responder with glioblastoma in the right parietal brain were imported into ScanIP 7.0 (Simpleware LTD., UK) for anatomical segmentation of the scalp, skull, dura, CSF, white matter, grey matter, brainstem, cerebellum, bilateral ventricle, gross total volume (GTV), necrotic core, and orbits. The co-registered image datasets from the 3 MRI sequences were used first for auto-segmentation followed by manual correction of some auto-segmented structures. Structures such as orbits, brainstem, and cerebellum were segmented and their associated physical properties were included mainly for spatial reference in the model. The GTV and necrotic core were both manually segmented by the treating physician. Transducer arrays were manually placed on the surface of the scalp, approximating as closely as possible to the standard visual model display as shown in the United States Food and Drug Administration's communication on the NovoTTF-100A system. Upon completion of the segmentation, a 3-dimensional finite element mesh was generated within ScanIP. This mesh was then imported into COMSOL Multiphysics (COMSOL, Burlington, Mass.), where material properties and boundary conditions were assigned as well as appropriate physics parameters were applied.

For the purpose of demonstrating the sensitivity of varying physical properties, such as electric conductivity and relative permittivity as well as the introduction or elimination of certain intracranial structures, only isotropic conductivity values were necessary to simplify the modeling process. Post-processing of data from the solved models was performed using Microsoft Excel, including generation of volume histograms EVH and SARVH. Area under the curve was computed using Simpson's Rule integration in MATLAB 2016 for electric fields ($E_{AUC}$) and SAR ($SAR_{AUC}$). The EVH was used in the comparison of electric field strength between different models and was referenced to (i) the percentage volume of a particular structure receiving at least 150 V/m ($V_{E150}$), (ii) the magnitude of electric field strength encompassing 95% of a particular structure's volume ($E_{95\%}$), (iii) the magnitude of electric field strength encompassing 50% of a particular structure's volume ($E_{50\%}$), and (iv) the magnitude of electric field strength encompassing 20% of a particular structure's volume ($E_{20\%}$). Similarly, the comparison of the rate of energy absorbed in different SARVH models was referenced to (i) the percentage volume of a particular structure receiving at least 7.5 W/kg ($V_{SAR7.5}$), (ii) the magnitude of SAR encompassing 95% of a particular structure's volume ($SAR_{95\%}$), (iii) the magnitude of SAR encompassing 50% of a particular structure's volume ($SAR_{50\%}$), and (iv) the magnitude of SAR encompassing 20% of a particular structure's volume ($SAR_{20\%}$).

Results

Electric Field Distribution of a Responder Treated with TTFields

Figure 3:
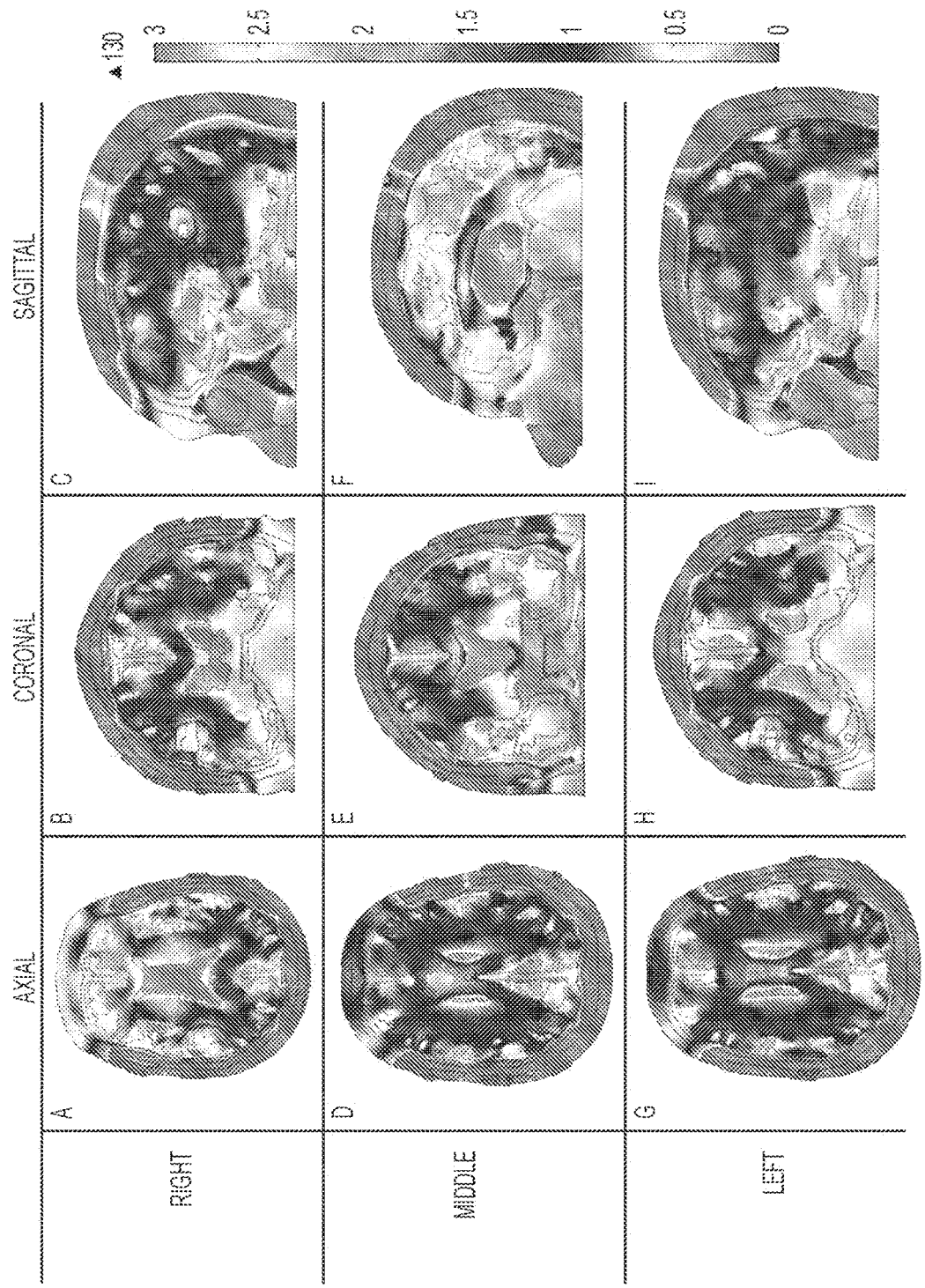
FIGS. 3A-3I show different views of the distribution of electric fields within a patient's brain. The electric field intensity is higher in the supratentorial brain than the infratentorial brain. Within the supratentorial brain, various parts of the sulci, the body of the corpus callosum, and the medial surface of the GTV (gross tumor volume) appear to have the highest electric field intensity.

A retrospective analysis of one glioblastoma patient, who responded to TTFields treatment, was performed by modeling the intracranial electric field distribution using finite element analysis as previously described. The responder had a glioblastoma in the right parietal lobe extending towards the bilateral ventricles with roughly 1.5 cm between the GTV and the lateral border of the right lateral ventricle. As expected the highest electric field intensity was seen within the sulci on the surface of the brain and there appeared to be a high-to-low gradient from the surface to the deeper regions of the brain (FIG. 3A-3I). In particular, the lowest intensity was seen in the inferior portion of the frontal (FIGS. 3C & 3I) and the temporal (FIGS. 3B & 3H) lobes. Furthermore, the body of the corpus callosum also had high electric field intensity, particularly in the regions between (FIG. 3D) and above the lateral ventricles (FIGS. 3E & 3F). The relatively higher conductivity of the cerebrospinal fluid located next to either side of the lesser conductive white matter probably created a higher capacitive reactance similar to a capacitor volume histogram; SARVH, specific absorption rate-volume histogram; $E_{AUC}$, electric field area under the curve; $V_{E150}$, volume covered with electric field intensity of 150 volts per meter; $E_{95\%}$, the electric field intensity encompassing 95% of volume; $E_{50\%}$, the electric field intensity encompassing 50% of volume; $E_{20\%}$, the electric field intensity encompassing 50% of volume; SAR, specific absorption rate; $SAR_{AUC}$, SAR area under the curve; $V_{SAR7.5}$, volume covered with specific absorption rate of 7.5 watts per kilogram; $SAR_{95\%}$, the magnitude of specific absorption rate encompassing 95% of volume; $SAR_{50\%}$, the magnitude of specific absorption rate encompassing 50% of volume; $SAR_{20\%}$, the magnitude of specific absorption rate encompassing 20% of volume.

TABLE 2

| | GTV | | | | | | | | | |
|---|---|---|---|---|---|---|---|---|---|---|
| Tissue Structure | $E_{AUC}$ | $V_{E150}$ | $E_{95\%}$ | $E_{50\%}$ | $E_{20\%}$ | $SAR_{AUC}$ | $V_{SAR7.5}$ | $SAR_{95\%}$ | $SAR_{50\%}$ | $SAR_{20\%}$ |
| Bilateral Ventricle | 14.7 | 0.0% | 5.7 | 9.8 | 25.2 | 4.0 | 13.1% | 0.7 | 2.6 | 5.3 |
| Brainstem | 35.7 | 0.0% | 23.6 | 36.3 | 44.0 | 1.2 | 0.0% | 1.2 | 2.1 | 2.6 |
| Cerebellum | 50.4 | 0.1% | 32.0 | 49.0 | 62.6 | 1.0 | 0.0% | 0.8 | 2 | 2.5 |
| CSF | 67.3 | 12.3% | 21.0 | 53.5 | 90.2 | 19.0 | 58.6% | 2.2 | 9.2 | 30 |
| Dura Matter | 108.3 | 35.7% | 25.4 | 86.2 | 169.8 | 8.2 | 32.3% | 1.3 | 4.9 | 17.1 |
| Gray Matter | 108.1 | 31.0% | 37.7 | 87.2 | 164.7 | 2.5 | 5.6% | 0.8 | 2.6 | 4.3 |
| GTV | 104.0 | 21.7% | 57.0 | 89.7 | 153.5 | 5.9 | 13.9% | 2.1 | 4.1 | 6.2 |
| Necrotic Core | 54.1 | 0.0% | 38.8 | 53.8 | 65.2 | 3.5 | 5.6% | 2.3 | 4.1 | 5.8 |
| Orbits | 5.7 | 0.0% | 4.2 | 6.2 | 7.8 | 0.0 | 0.0% | 0.5 | 0.8 | 0.9 |
| Scalp | 596.0 | 71.2% | 24.8 | >1000 | >1000 | 8.7 | 21.0% | 0.1 | 0.9 | 8.3 |
| Skull | 537.8 | 67.1% | 24.6 | 437.2 | >1000 | 31.8 | 38.1% | 0.6 | 2.5 | 42.8 |
| White Matter | 126.9 | 45.3% | 48.7 | 137.0 | 169.8 | 2.2 | 2.4% | 0.9 | 2.7 | 4.3 | that retains a higher electric field intensity within the white matter. Lastly, the medial portion of GTV in the right parietal lobe also possessed higher electric field intensity, and this could be a function of the higher conductivity of the necrotic core within the GTV on one side and the cerebrospinal fluid in the right lateral ventricle on the other side also resulting in a higher reactive capacitance.

Figure 4A:
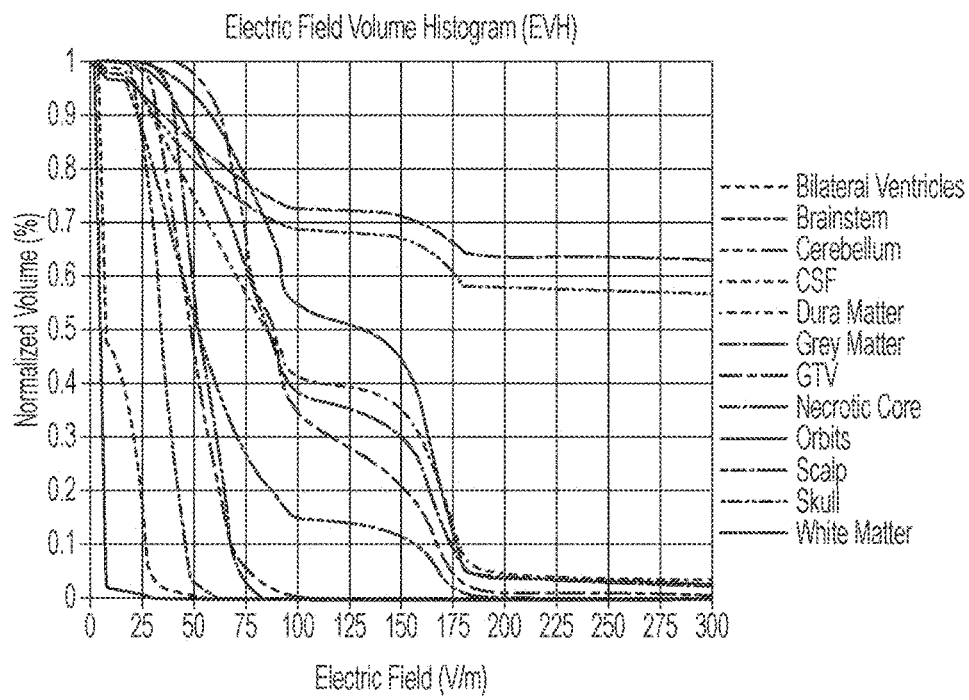
FIGS. 4A-4D show volume histograms EVH and SARVH and electric field and specific absorption rate distribution maps, respectively. The EVH (FIG. 4A), SARVH (FIG. 4B), electric field map (FIG. 4C), and SAR map (FIG. 4D) were generated using the transducer array placement as outlined in FIG. 5E. The highest $E_{AUC}$ was found at the scalp and skull, while the lowest was detected at the orbits, bilateral ventricles and brainstem. The highest $SAR_{AUC}$ was found at the layer of cerebrospinal fluid between cortex and dura, the GTV (gross tumor volume), and skull, while the lowest was found in the orbits, cerebellum, and the orbits.
Figure 4B:
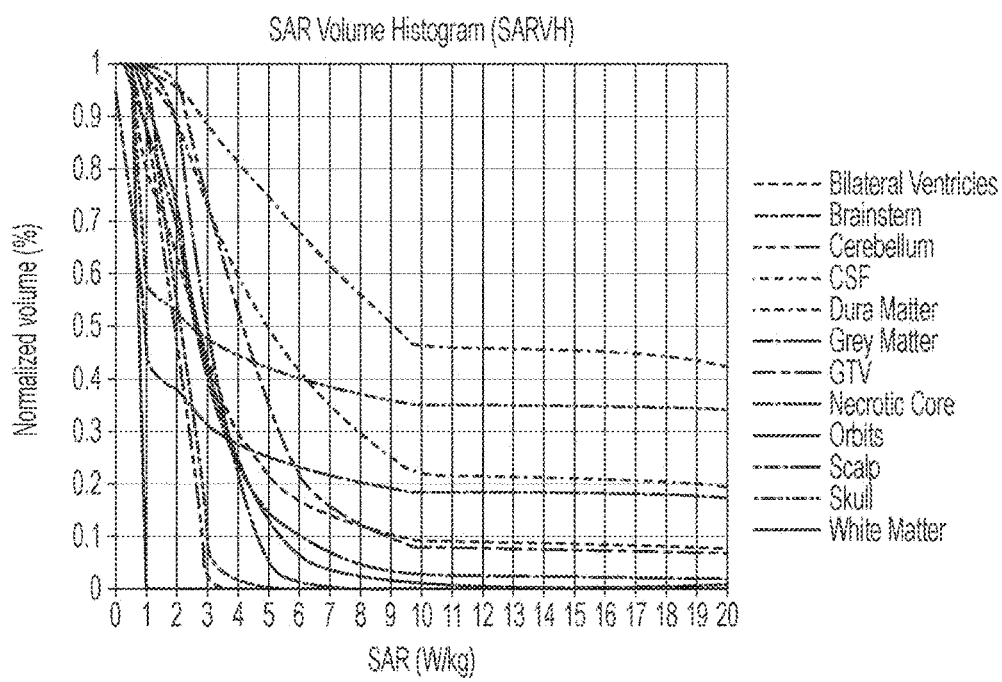
Figure 4D:
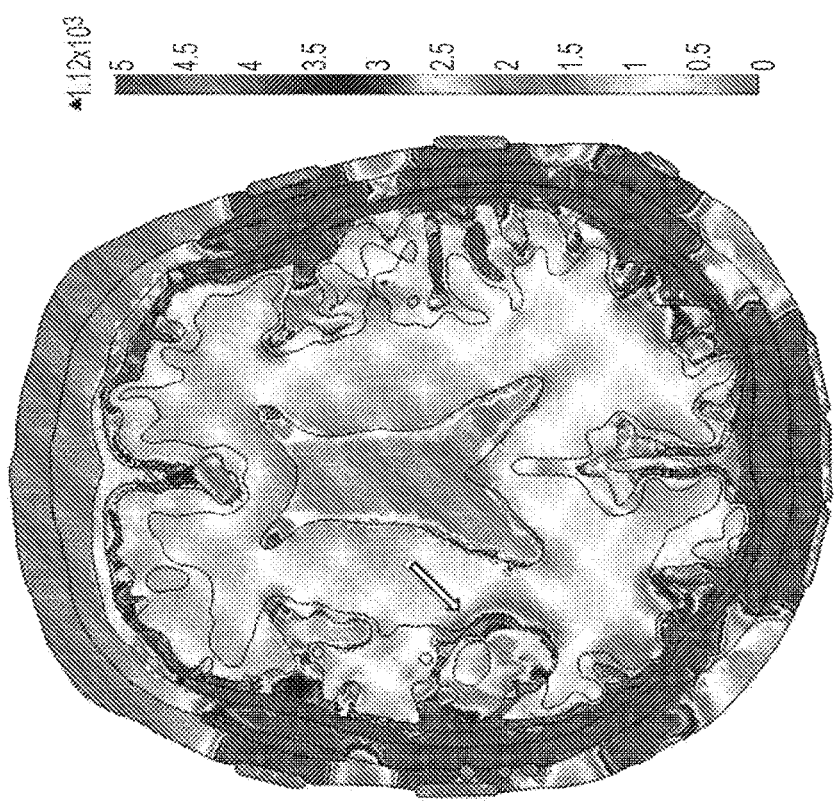
Figure 4C:
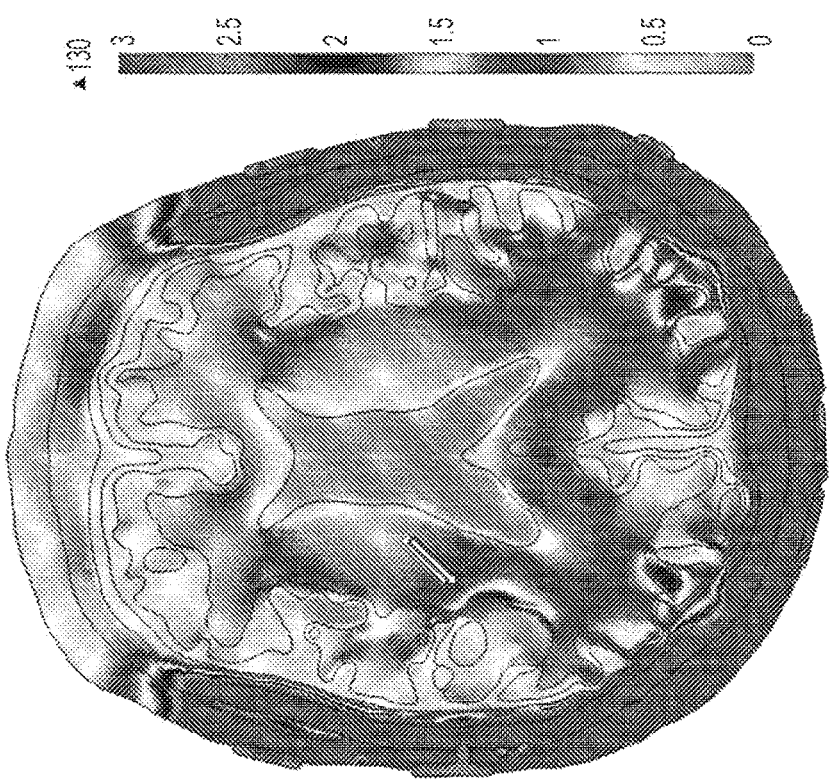

To investigate the strength of electric field and the rate of energy deposited into the GTV and various intracranial structures, EVH and SARVH were generated for the comparison between models that use the primary position for transducer array placement as outlined in FIG. 5E and incorporate the isotropic conductivity and relative permittivity values listed in Table 1. As expected, the highest $E_{AUC}$ was found at the scalp and skull while the lowest was located at the orbits, bilateral ventricles, and brainstem (FIGS. 4A & 4C). In the GTV, 95% of the volume had an electric field intensity of >50 V/m while 50% had >80 V/m and 20% has >150 V/m (FIG. 4A). Because at least 20% of the GTV volume had a minimum of 150 V/m of electric field coverage (Table 2), the $V_{E150}$ volume and $E_{50\%}$ magnitude were used as means of comparing different modeling outcomes in subsequent analyses. Similarly, the highest $SAR_{AUC}$ was found at the layer of cerebrospinal fluid between cortex and dura, the GTV, and skull, while the lowest were located in the orbits, cerebellum, and brainstem (FIGS. 2B &2D). Because at least 15% of the GTV volume had a SAR of at least 7.5 W/kg (Table 2), the $V_{SAR7.5}$ volume and $SAR_{50\%}$ magnitude were used as means of comparing different modeling outcomes in subsequent analyses.

Figure 6A:
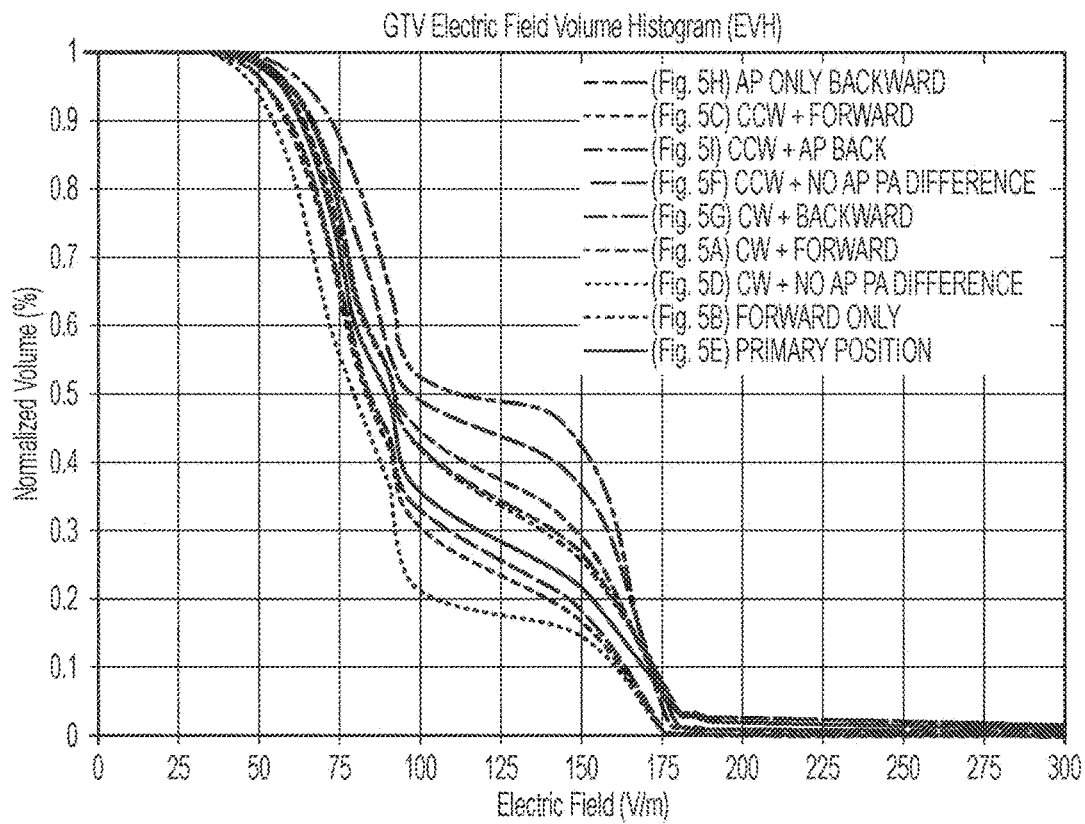
FIGS. 6A-6D show EVH and SARVH generated from array displacement analysis. Electric field coverage of the GTV was highly variable between 100 to 150 V/m, ranging from only 20% volume having 100 V/m with clockwise rotation of the lateral arrays and no displacement of the anterior-posterior arrays (red curve), to >40% volume having at least 150 V/m when the lateral arrays were rotated in a counter clockwise fashion and the anterior array was moved backward (green curve) (A). However, the variability in the magnitude of SAR encompassing 50% of the GTV, as represented by the magnitude of $SAR_{50\%}$, was low and it ranged between 3 and 6 W/kg (C). For the necrotic core of the tumor, the electric field (C) and SAR magnitude (D) variability at the GTV was also smaller. Each curve corresponds to specific array placement position as shown in FIGS. 5A-5I.
Figure 6B:
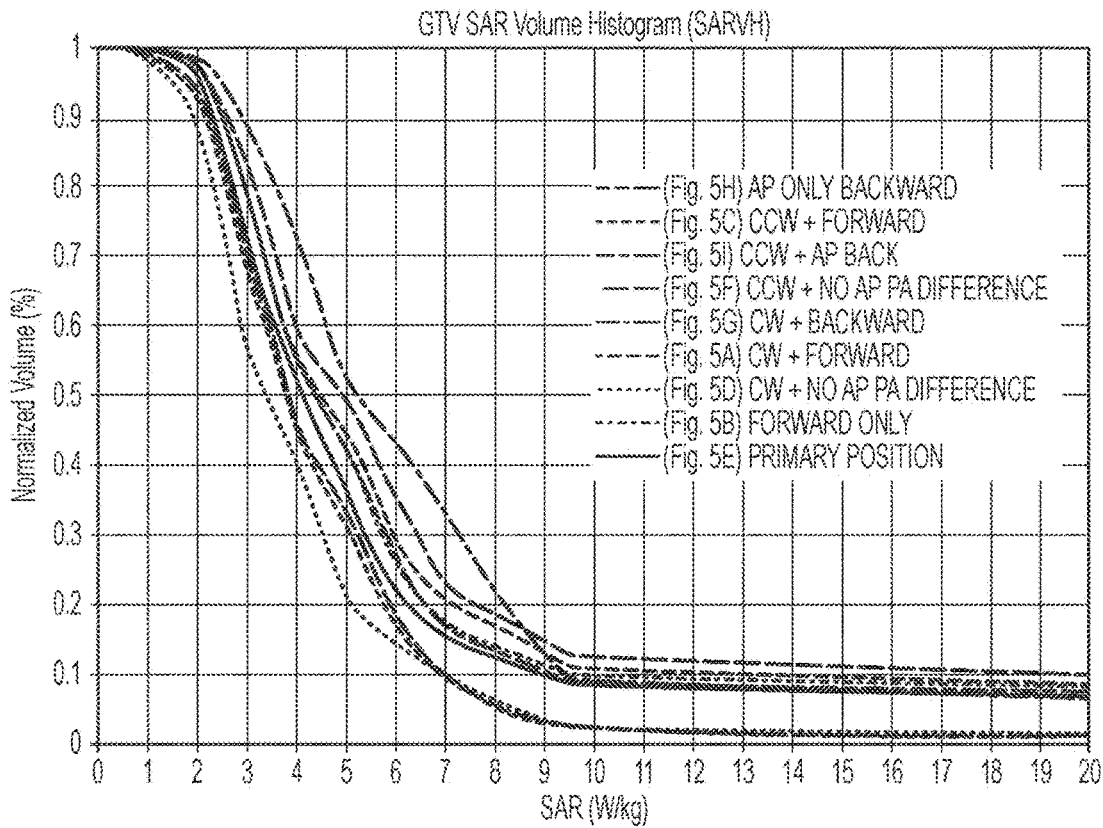
Figure 6C:
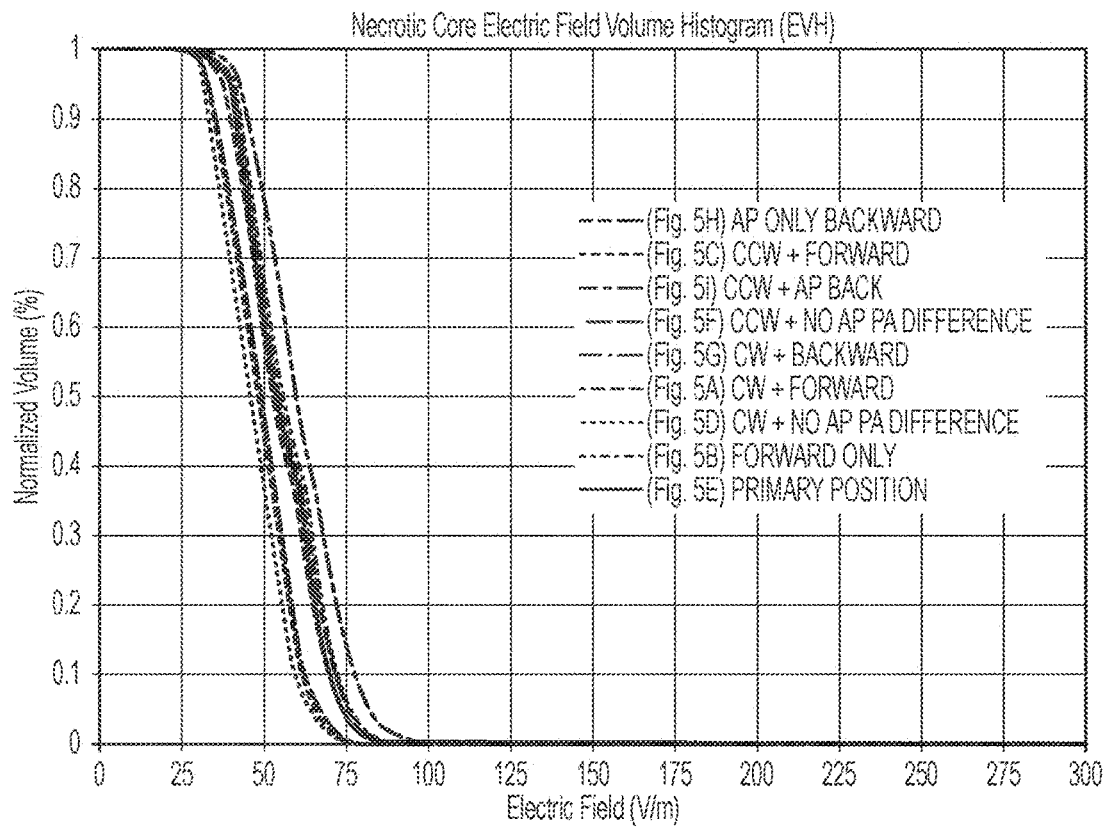
Figure 6D:
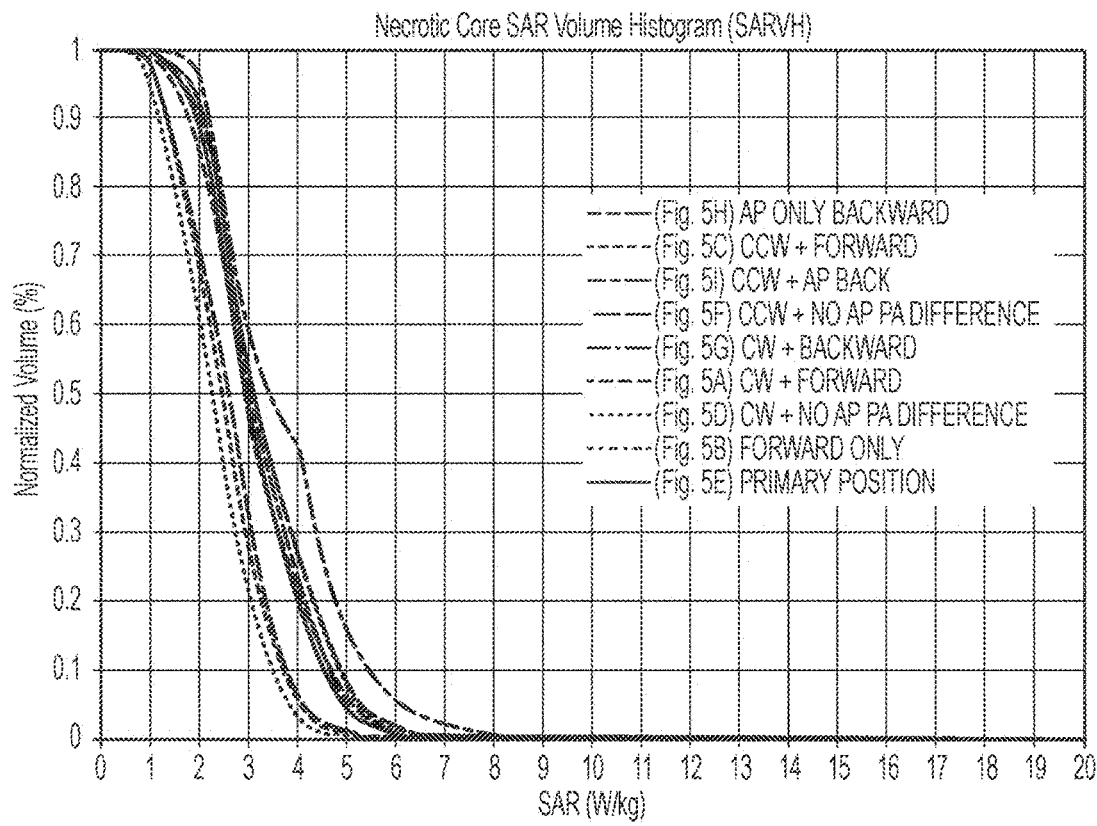

Table 2, below, provides values for the electric field and specific absorption rate distribution at the GTV and other anatomical structures as shown in EVH and SARVH from FIG. 4. GTV, gross tumor volume; EVH, electric field- Disposition Analysis of Transducer Array Placement Because the placement of transducer arrays can be shifted during each array exchange on treatment, we determined whether or not the disposition of the arrays can alter electric field coverage and rate of energy deposition in the GTV. To model the effects of shifting array positions at different locations on the scalp, each of the 9 disks in each array were manually drawn to scale and in contact with the surface of the scalp in the configuration of the primary position as shown in FIG. 5E. In each disposition modeling, the disks in each array were positioned in aggregate by a 2-cm deviation from the primary position. The lateral arrays were then shifted in clockwise and counter clockwise configurations while the anterior-posterior arrays were shifted in the forward and backward positions, resulting in 8 additional configurations (FIG. 5, except for FIG. 5E [primary position]). The posterior array in all cases was not moved inferiorly due to the fact that the patient's image dataset was truncated at the occiput, and thus there was not sufficient occipital anatomy to shift the posterior array inferiorly. Still, there was high variance in electric field coverage of the GTV between 100 to 150 V/m, ranging from only 20% volume having 100 V/m with clockwise rotation of the lateral arrays and no displacement of the anterior-posterior arrays (FIG. 6A, curve corresponding to FIG. 3D) to >40% volume having at least 150 V/m when the lateral arrays were rotated in a counter clockwise fashion and the anterior array was moved backward (FIG. 6A, curve corresponding to FIG. 3I). However, the variability in SAR of the GTV, as represented by the magnitude of $SAR_{50\%}$, was low and it ranged between 3 and 6 W/kg (FIG. 6B). For the necrotic core of the tumor, there was also a similar but smaller variance in the electric field coverage (FIG. 6C) and its corresponding SAR magnitude (FIG. 6D).

Sensitivity Analysis of the Conductivity of the GTV and the Necrotic Core

Figure 7B:
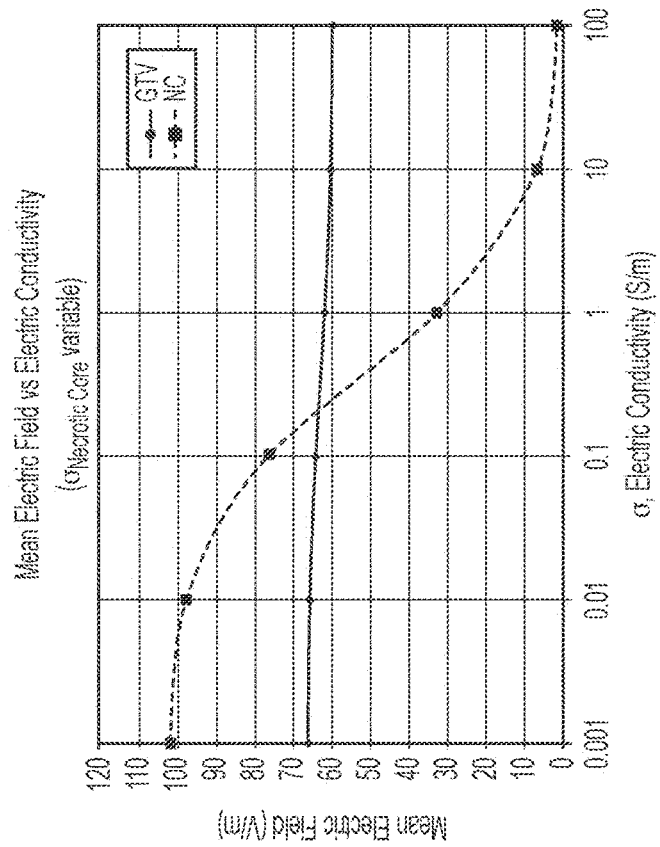
FIGS. 7A-7D show plots of sensitivity analysis of conducivity of GTV and necrotic core. When the electric conductivity of the necrotic core was held constant and the electric conductivity of the GTV (gross tumor volume) was varied, the mean electric field strength within the necrotic core rose 600% from 5 to 30 V/m when the conductivity of the GTV decreased from 100 to 1 S/m, but further increase was markedly attenuated when the conductivity was lowered from 1 to 0.001 S/m (FIG. 7A). The mean SAR increased from 0 to 1.8 W/kg when the conductivity of the GTV was decreased from 100 to 1 S/m, but further increase was negligible when the conductivity was lowered from 1 to 0.001 S/m (FIG. 7C). When the electric conductivity of the GTV was held constant and the electric conductivity of the necrotic core was varied from 100 to 1 S/m, there was negligible change in the mean electric field strength in the GTV; but there was up to a 10% increase in mean electric field strength of the GTV when the electrical conductivity of the necrotic core was lowered from 1 to 0.001 S/m (FIG. 7B). But the change in mean SAR of the GTV was insignificant when the necrotic core conductivity was varied from 100 to 0.001 S/m (FIG. 7D). GTV, gross tumor volume; V/m, volt per meter; S/m, siemens per meter; W/kg, watt per kilogram; SAR, specific absorption rate.
Figure 7A:
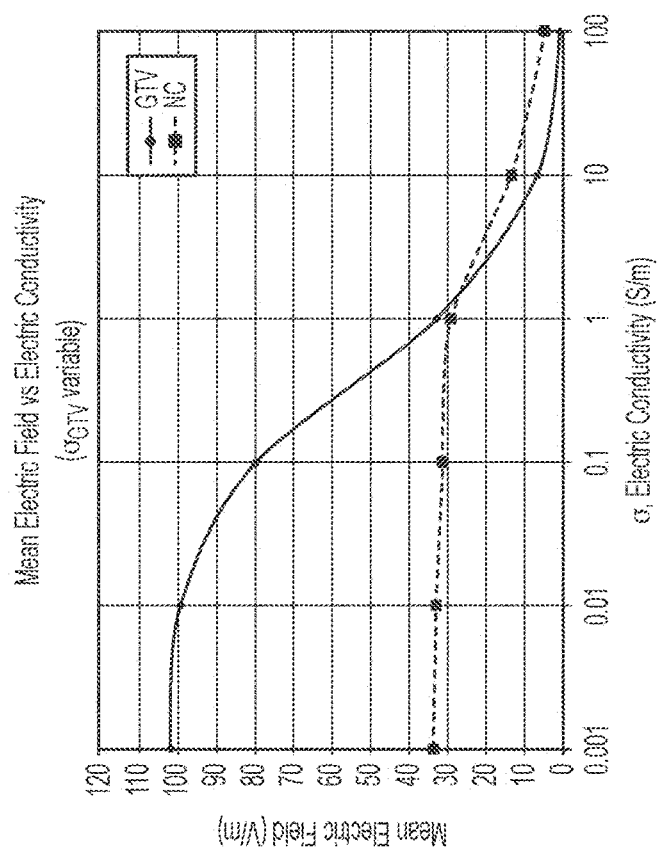
Figure 7D:
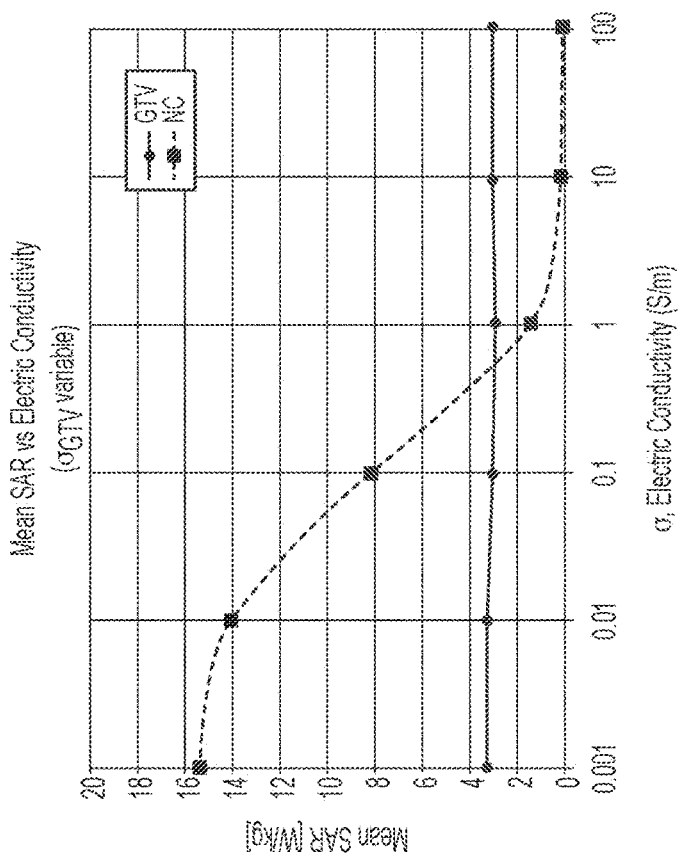
Figure 7C:
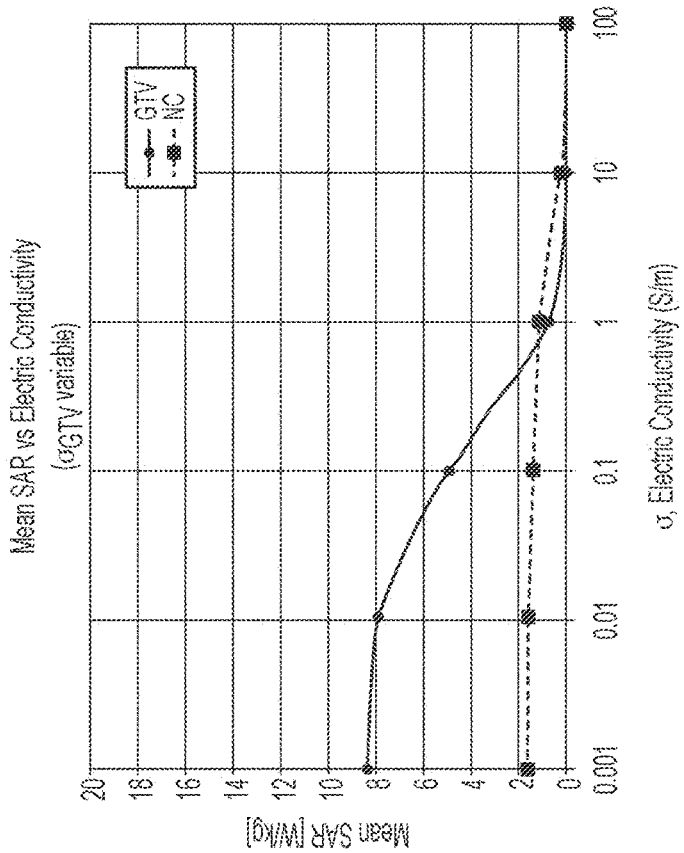

The strength of the electric field penetrating the GTV most likely depends on its dielectric properties, in particular the electrical conductivity and relative permittivity. Our previous modeling found that the electric field intensity at the GTV is more sensitive to changes in its electrical conductivity than its relative permittivity characteristics. However, a tumor frequently has a necrotic component that contains liquefied cellular products or exudates from adjacent highly permeable vasculature. The fluid component of this necrotic core can potentially influence the electric field strength within the GTV. To investigate the relationship between the GTV and necrotic core, the electric conductivity of the GTV was altered from 100 to 0.001 S/m while the conductivity of the necrotic core was kept constant. The mean electric field strength within the necrotic core rose 600% from 5 to 30 V/m when the conductivity of the GTV decreased from 100 to 1 S/m, but further increase was markedly attenuated when the conductivity was lowered from 1 to 0.001 S/m (FIG. 7A). Similarly, the mean SAR increased from 0 to 1.8 W/kg when the conductivity of the GTV decreased from 100 to 1 S/m, but further increase was negligible when the conductivity was lowered from 1 to 0.001 S/m (FIG. 7C). In contrast, when the electric conductivity of the necrotic core was varied from 100 to 1 S/m, there was negligible change in the mean electric field strength in the GTV; however, there was up to a 10% increase in mean electric field strength of the GTV when the electrical conductivity of the necrotic core was lowered from 1 to 0.001 S/m (FIG. 7B). But the change in mean SAR of the GTV was insignificant when the necrotic core conductivity was varied from 100 to 0.001 S/m (FIG. 7D).

Figure 8A:
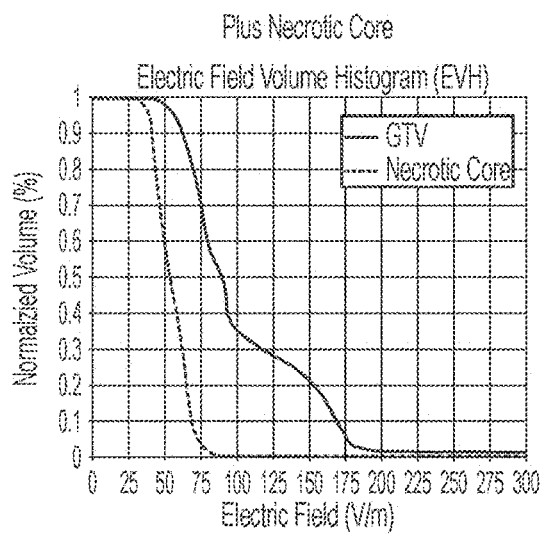
FIGS. 8A-8F show sensitivity analysis for electric field strength and specific absorption rate with or without the necrotic core. EVH (FIG. 8A) and SARVH (FIG. 8C) were modeled with the necrotic core, which consisted of highly conductive fluid. When the necrotic core was replaced with poorly conductive tissue, such as white matter, the electric field coverage and specific absorption rate were increased as shown in the EVH (FIG. 8B) and SARVH (FIG. 8D), respectively. The electric field diagrams showed differences in the electric field coverage at the GTV with (FIG. 8E) and without (FIG. 8F) the necrotic core. EVH, electric field-volume histogram; SARVH, specific absorption rate-volume histogram.
Figure 8B:
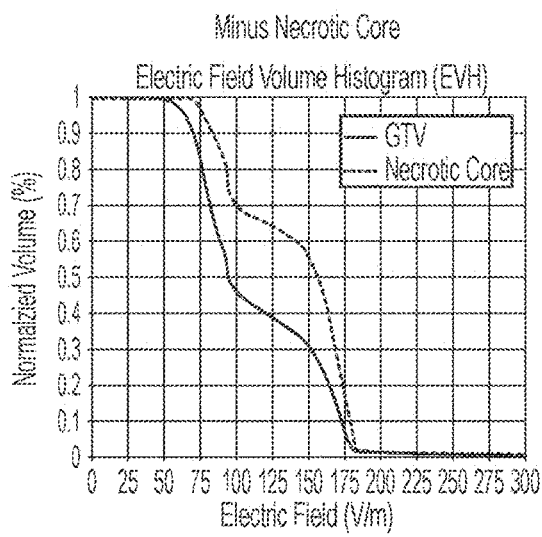
Figure 8C:
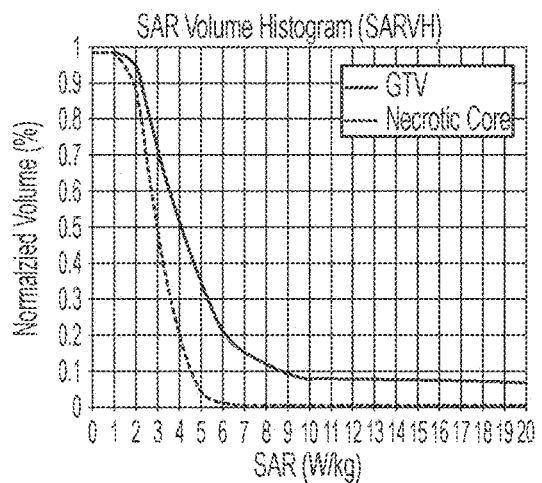
Figure 8D:
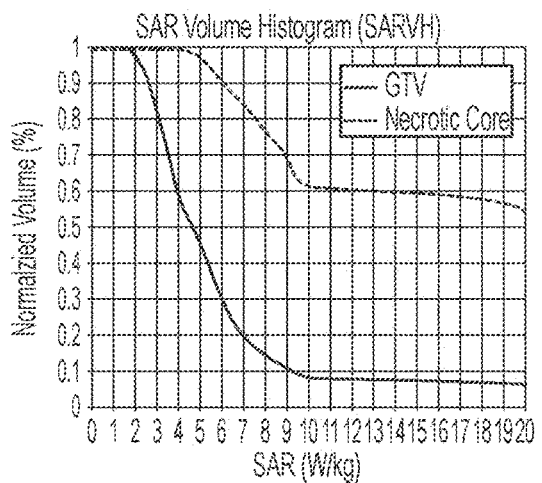
Figure 8E:
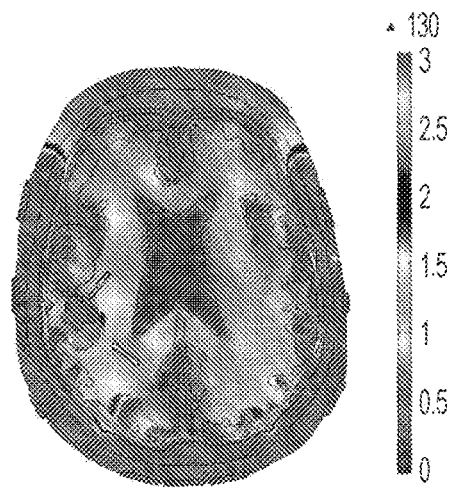
Figure 8F:
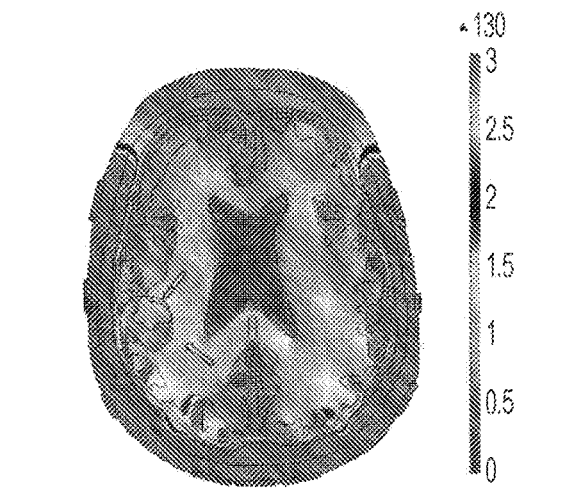

To determine the electric field coverage of GTV as influenced by the conductivity of the necrotic core, both EVH and SARVH were constructed as the GTV was modeled with or without the necrotic core. When highly conductive fluid in the necrotic core was replaced with electrical conductivity and relative permittivity of white matter, the $V_{E150}$ of the GTV shifted from 20% to 30% (FIGS. 8A & 8B) and the corresponding $V_{SAR7.5}$ increased from 13% to 15% (FIGS. 8C & 8D), indicating that electric field and SAR coverage of the GTV increased as the highly conductive fluid within the necrotic core is replaced with less conductive materials. Because the dielectric properties of GTV and necrotic core probably vary among individual patients, the findings here indicate that measuring the individualized conductivity and permittivity values may have relevance in modeling TTFields in cancer patients.

The Influence of Cerebrospinal Fluid on GTV

Figure 9B:
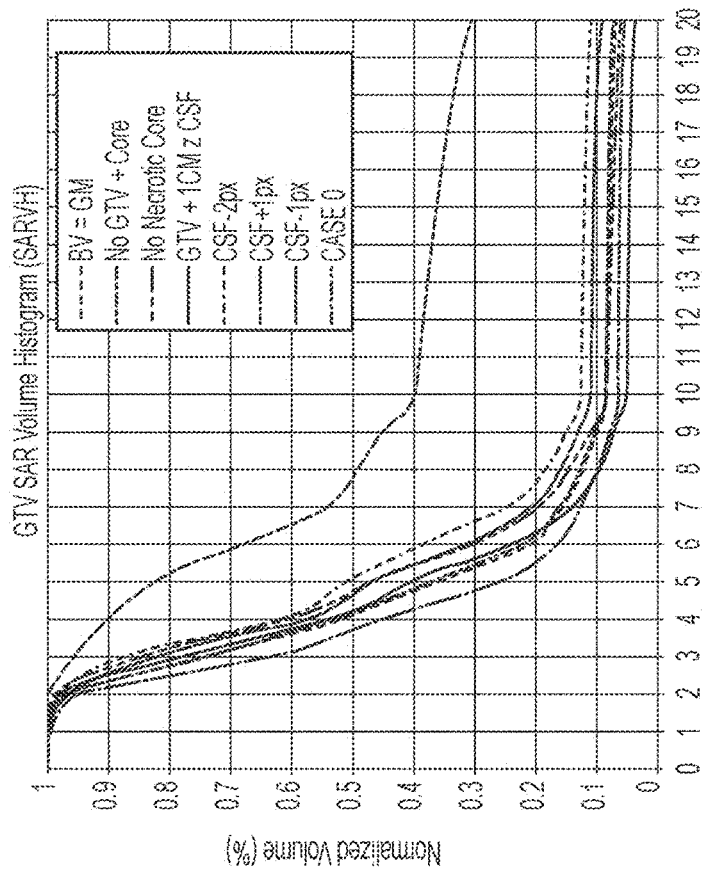
FIGS. 9A-9C show influence of cerebrospinal fluid on the electric field strength and specific absorption rate at the GTV and necrotic core. The layer of cerebrospinal fluid was altered by +1, −1, and −2 pixels at the convexity of the brain and the respective EVH (FIG. 9A) and SARVH (FIG. 9B) at the GTV were generated. The electric field quantities $E_{AUC}$, $V_{E150}$, and $E_{50\%}$, as well as quantities for the specific absorption rate $SAR_{AUC}$, $V_{SAR7.5}$, and $SAR_{50\%}$, all increased progressively when the cerebrospinal fluid space was narrowed progressively from +1 pixel to −1 pixel, and then to −2 pixels on the convexity of the brain. GTV, gross tumor volume; EVH, electric field-volume histogram; SARVH, specific absorption rate-volume histogram; $E_{AUC}$, electric field area under the curve; $V_{E150}$, volume covered with electric field intensity of 150 volts per meter; and $E_{50\%}$, the electric field intensity encompassing 50% of volume; SAR, specific absorption rate; $SAR_{AUC}$, SAR area under the curve; $V_{SAR7.5}$, volume covered with specific absorption rate of 7.5 watts per kilogram; $SAR_{50\%}$, the magnitude of specific absorption rate encompassing 50% of volume.
Figure 9A:
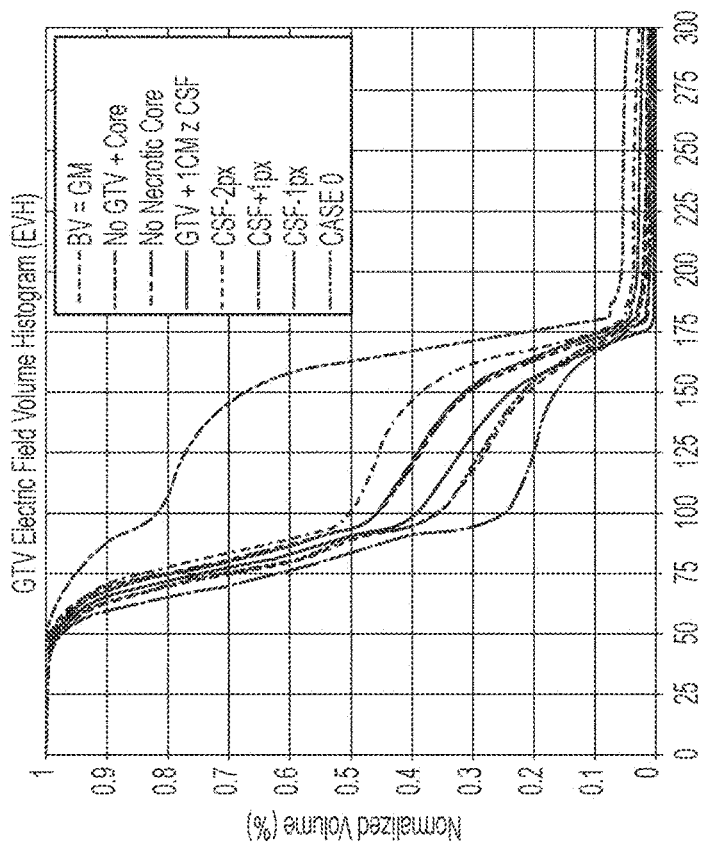
Figure 9C:
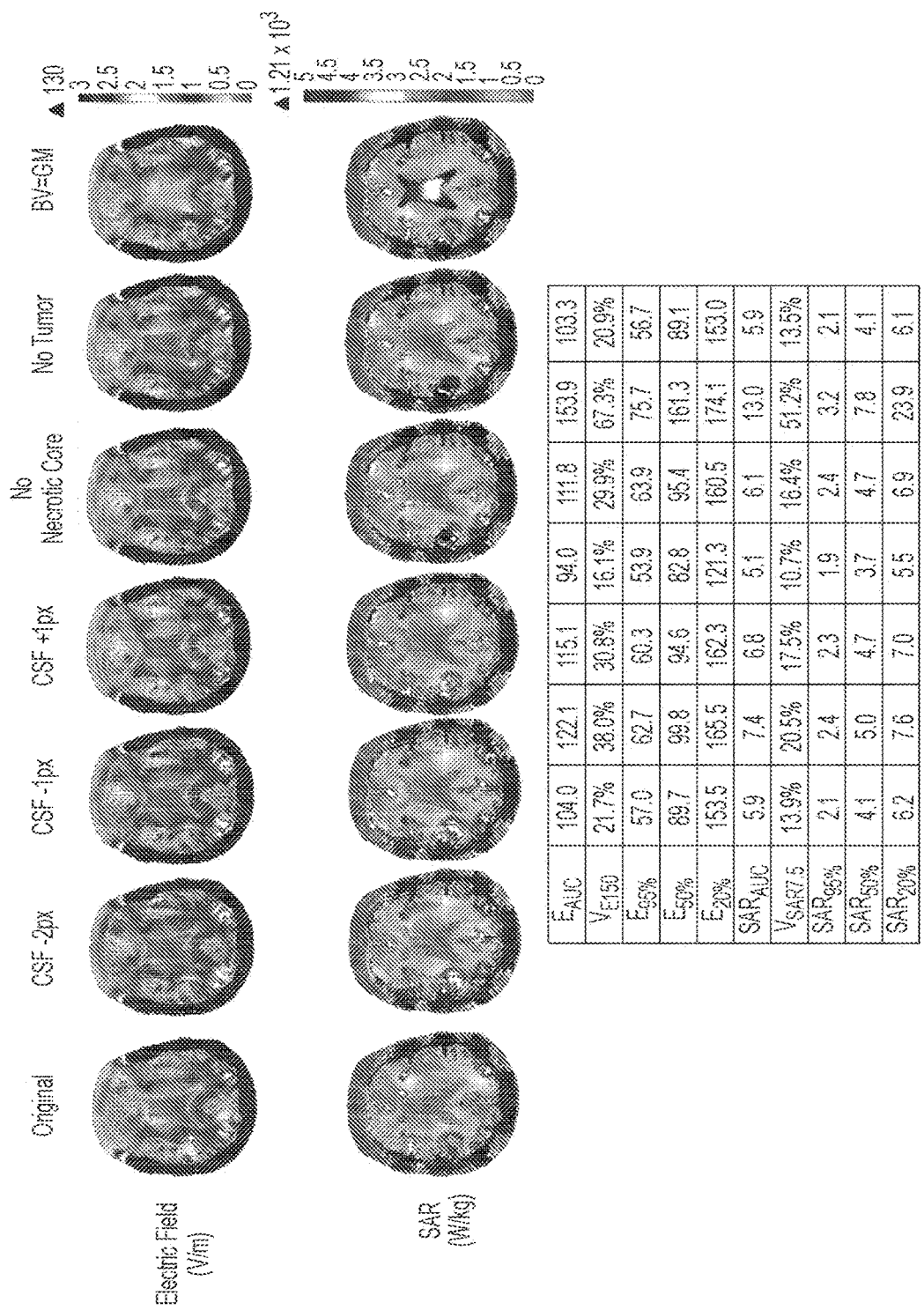

Since cerebrospinal fluid is a highly conductive media and it is in close proximity to the GTV, we determined whether the cerebrospinal fluid on the surface of the brain and inside the ventricles could influence the electric field and SAR coverage of the GTV. First, 1 pixel of CSF was added on the surface and then in separate models, 1 or 2 pixels of CSF were subtracted from the surface of the original brain to investigate the effect on the electric field distribution within the GTV. Indeed, the $E_{AUC}$, $VE_{150}$, and $E_{50\%}$ all increased progressively when the CSF space was narrowed progressively from +1 pixel to -2 pixels on the convexities of the brain. Specifically, $E_{AUC}$ increased from 94.0 V/m at +1 pixel to 115.1 V/m at -1 pixel, and to 122.1 V/m at -2 pixels (FIG. 9C). Similarly, the rate of energy deposited in the GTV, as represented by $SAR_{AUC}$, $V_{SAR7.5}$, and $SAR_{50\%}$, when the CSF space was narrowed progressively from +1 pixel to -2 pixels on the convexities of the brain. In particular, $SAR_{AUC}$ increased from 5.1 W/kg at +1 pixel, to 6.8 W/kg at -1 pixel, and to 7.4 W/kg at -2 pixels (FIG. 9C). Therefore, increased CSF space at the convexity shunts electric field and energy away from the brain while decreased CSF space allows a higher intensity of electric field and SAR to penetrate the brain.

The Influence of Tumor Geometry on EVH and SARVH

Figure 10B:
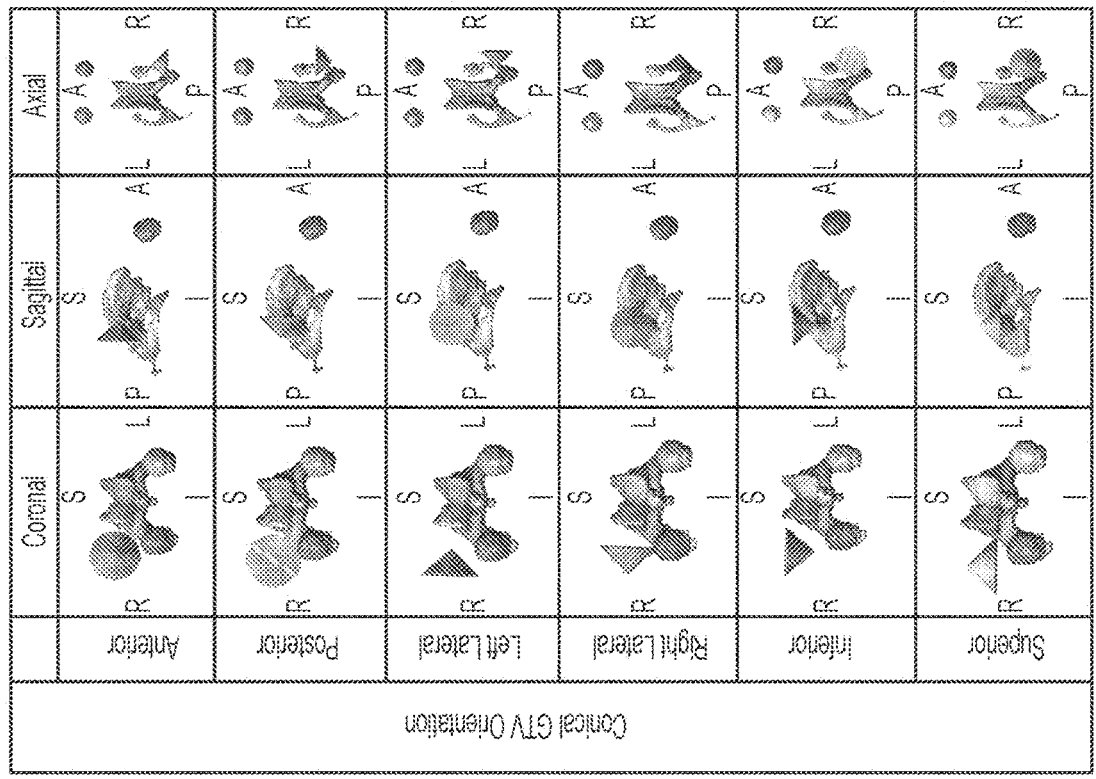
FIGS. 10A-10B show geometric analysis of GTV on EVH and SARVH. The glioblastoma was represented by standard relatively symmetric geometric solids, including cube, cylinder, sphere, and icosahedron, for studying changes in electric fields distribution and specific absorption rate in the GTV (FIG. 10A). The conical shape was also chosen because it is relatively more asymmetrical. Its position in the brain, as represented by the anterior, posterior, left lateral, right lateral, inferior, and superior orientations, were also used for studying changes in electric fields distribution and energy deposition in the GTV (FIG. 10B). GTV, gross tumor volume EVH, electric field-volume histogram; SARVH, specific absorption rate-volume histogram.
Figure 10A:
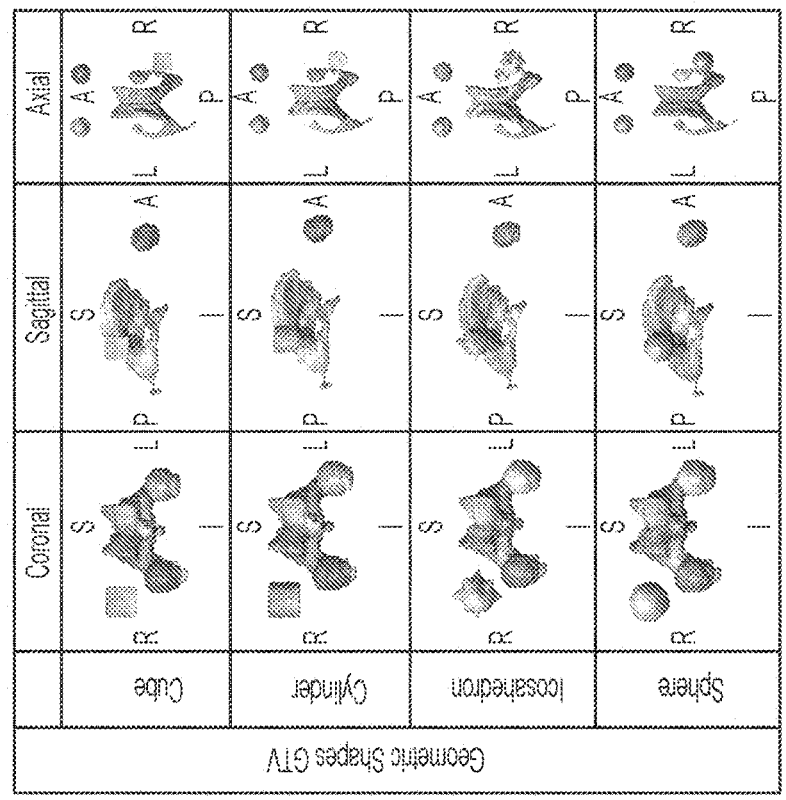

The influence of tumor geometry on the electric field and specific absorption rate was also determined. The original GTV was kept intact as segmented in the patient's model, and was used to compare with GTVs of other standard geometric solids, while keeping the center of each GTV at the same location. All other parameters, such as array position, and conductivity of tissue remained the same (FIG. 5E and Table 1). Standard geometric solids, including cube, cylinder, sphere, icosahedron, and cone, were used to represent the shape of the tumor for studying changes in electric fields distribution and energy deposition in the GTV (FIGS. 10A and 10B). To simplify the comparisons, the necrotic core properties across all models, including the original brain model, were set equal to the GTV; thus, the GTV studied in this section is essentially GTV and necrotic core combined into one entity. In addition, it was of particular interest how the electric fields would be distributed depending on the orientation of the conical solid. The conical solid was therefore rotated about the geometric centroid of the original patient's GTV, with the tip of the solid pointing in 6 different directions: patient's anterior, posterior, left, right, superior and inferior. Likewise, the centroid of the remaining standard geometric solids was equal to that of the patient's original GTV as well.

Figure 11B:
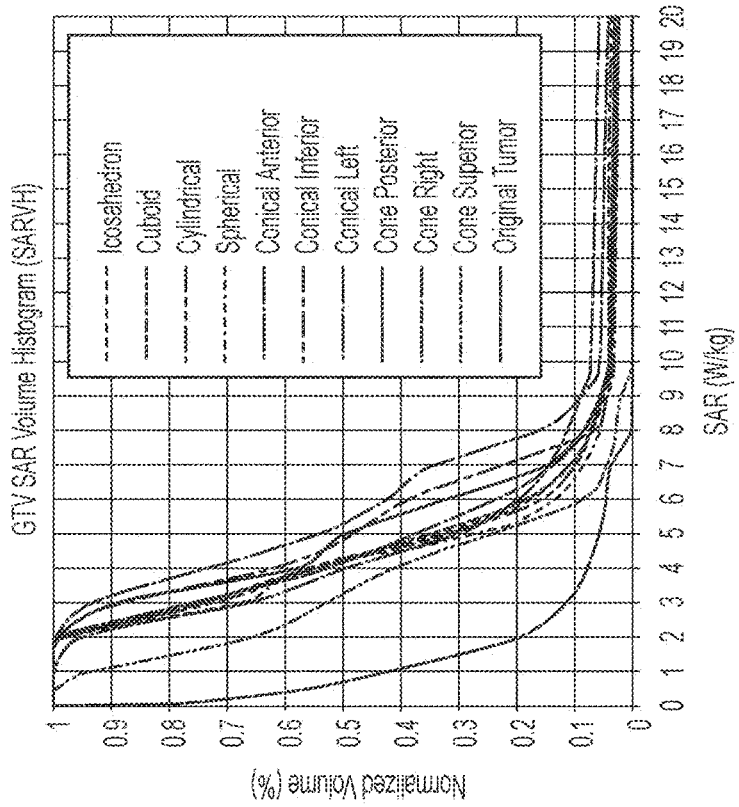
Figure 11A:
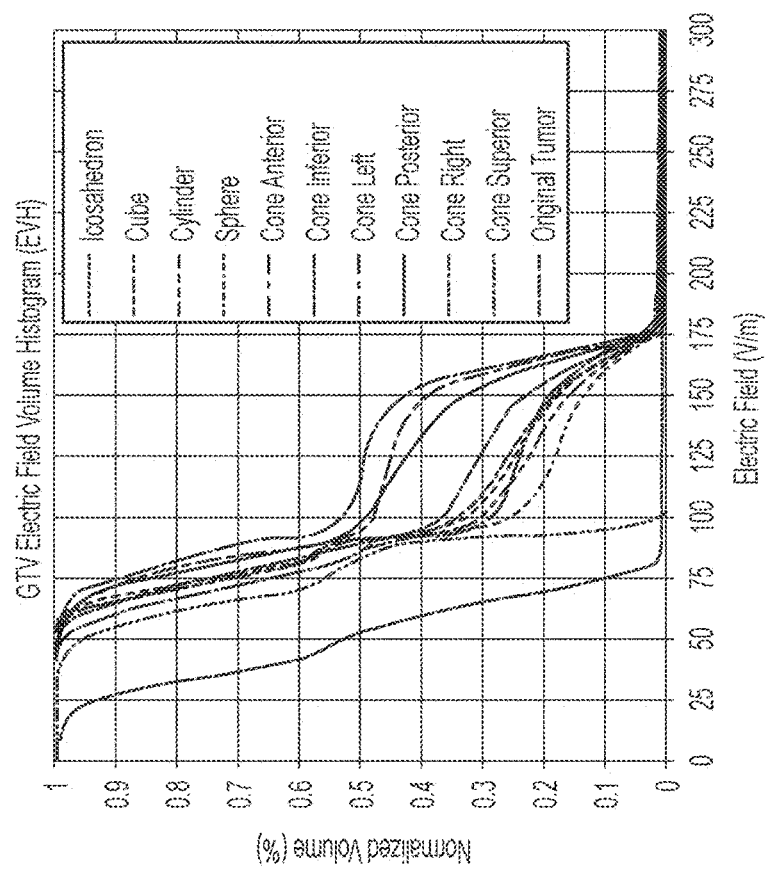

Compared to the original tumor geometry, symmetric, less angulated geometries had a tendency to associate with a lower basal level of electric fields, as shown by lower values in $E_{AUC}$ and $E_{20\%}$, and diminished energy absorption, as shown by $SAR_{AUC}$ and $SAR_{20\%}$ (FIGS. 11A-11C). In particular, the cylindrical and spherical GTVs had lower $E_{AUC}$ and $E_{20\%}$, as well as $SAR_{AUC}$ and $SAR_{20\%}$, than that for the cube and icosahedron, likely due to the fact that the latter ones had more angulated corner structures. For the lesser symmetric geometric shapes, such as a cone, the orientation in the 3-dimensional space of the brain was important. The $E_{AUC}$ and $E_{20\%}$, as well as $SAR_{AUC}$ and $SAR_{20\%}$, had the lowest values when the cone was oriented superiorly but highest when positioned anteriorly (FIG. 10B & FIG. 11C). The highest values of $E_{AUC}$ 122.0 V/m and $E_{20\%}$ 163.9 V/m, as well as $SAR_{AUC}$ 6.5 W/kg and $SAR_{20\%}$ 7.8 W/kg, were found when the conical GTV was pointing anteriorly, with the flat surface facing orthogonally to the lateral ventricle.

Table 3, shown below, shows values for electric field and rate of energy deposition parameters at the GTV as shown FIG. 10 based on geometric analysis. GTV, gross tumor volume; EVH, electric field-volume histogram; SARVH, specific absorption rate-volume histogram; $E_{AUC}$, electric field area under the curve; $V_{E150}$, volume covered with electric field intensity of 150 volts per meter; $E_{95\%}$, the electric field intensity encompassing 95% of volume; $E_{50\%}$, the electric field intensity encompassing 50% of volume; $E_{20\%}$, the electric field intensity encompassing 50% of volume; SAR, specific absorption rate; $SAR_{AUC}$, SAR area under the curve; $V_{SAR7.5}$, volume covered with specific absorption rate of 7.5 watts per kilogram; $SAR_{95\%}$, the magnitude of specific absorption rate encompassing 95% of volume; $SAR_{50\%}$, the magnitude of specific absorption rate encompassing 50% of volume; $SAR_{20\%}$, the magnitude of specific absorption rate encompassing 20% of volume.

| | $E_{AUC}$ | $V_{E150}$ | $E_{95\%}$ | $E_{50\%}$ | $E_{20\%}$ | $SAR_{AUC}$ | $V_{SAR7.5}$ | $SAR_{95\%}$ | $SAR_{50\%}$ | $SAR_{20\%}$ |
|---|---|---|---|---|---|---|---|---|---|---|
| Nominal Symmetric Geometric Shapes GTV | 104.0 | 21.7% | 57.2 | 89.9 | 153.6 | 5.9 | 13.9% | 2.1 | 4.1 | 6.2 |
| Cube | 101.1 | 18.5% | 62.8 | 90.8 | 146.1 | 5.0 | 8.7% | 2.3 | 4.2 | 5.9 |
| Cylinder | 99.5 | 15.8% | 63.0 | 91.2 | 135.0 | 5.1 | 8.3% | 2.3 | 4.2 | 5.7 |
| Icosahedron | 101.1 | 17.9% | 64.5 | 92.1 | 144.2 | 5.0 | 8.7% | 2.3 | 4.3 | 5.8 |
| Sphere | 96.7 | 13.7% | 63.7 | 92.3 | 115.0 | 4.8 | 7.0% | 2.3 | 4.3 | 5.4 |
| Asymmetric Conical GTV (orientation) | | | | | | | | | | |
| Anterior | 122.0 | 42.6% | 71.1 | 109.2 | 163.9 | 6.5 | 25.3% | 2.8 | 5.3 | 7.8 |
| Posterior | 113.9 | 32.8% | 66.7 | 98.6 | 160.3 | 5.5 | 11.2% | 2.6 | 5.0 | 6.7 |
| Left Lateral | 99.4 | 19.3% | 55.8 | 86.3 | 147.6 | 5.5 | 12.5% | 2.0 | 3.9 | 5.9 |
| Right Lateral | 104.3 | 23.4% | 61.3 | 89.5 | 155.1 | 5.3 | 10.6% | 2.3 | 4.2 | 6.3 |
| Inferior | 117.1 | 38.9% | 66.1 | 96.2 | 162.7 | 5.7 | 12.9% | 2.6 | 4.9 | 7.1 |
| Superior | 77.9 | 0.4% | 51.0 | 82.7 | 94.9 | 3.5 | 3.4% | 0.9 | 3.2 | 5.2 |

Discussion

As it is being used to treat glioblastoma, TTFields at 200 kHz permeate the patient brain according to the laws of physics, including Gauss' law, Coulomb's law, continuity equation and capacitance. Our modeling of these fields using the finite element method reveals that the intensity of TTFields are highest at the sulci, genu of the corpus callosum, and at the medial surface of the GTV facing the lateral ventricle. To better assess quantitatively the electric field distribution and rate of energy deposition within the brain, volume histograms were constructed for the electric fields and SAR. This is the first use of both EVH and SARVH to view TTFields distribution and rate of energy deposition within the patient brain. Both EVH and SARVH can also facilitate the quantitative comparison of intracranial TTFields between patients, using pre-specified values at the GTV, such as $E_{AUC}$, $V_{E150}$, $E_{95\%}$, $E_{50\%}$, and $E_{20\%}$ for TTFields distribution as well as $SAR_{AUC}$, $V_{SAR7.5}$, $SAR_{95\%}$, $SAR_{50\%}$, and $SAR_{20\%}$ for rate of energy deposition. $E_{AUC}$ represents the aggregate electric fields as represented by the area under the curve within the GTV and $V_{E150}$ is the volume of distribution for the electric field intensity at least 150 V/m on the histogram. Similarly, $SAR_{AUC}$ also represents the aggregate rate of energy deposited as represented by the area under the curve within the GTV and $V_{SAR7.5}$ is the volume of distribution for SAR at 7.5 W/kg on the histogram. In addition, $E_{95\%}$, $E_{50\%}$, and $E_{20\%}$ are data points on the EVH curve that represent the electric field intensity that covers 95%, 50% and 20% of the GTV, while $SAR_{95\%}$, $SAR_{50\%}$, and $SAR_{20\%}$ are data points on the SARVH that represent the rate of energy deposited in 95%, 50% and 20% of the GTV. Collectively, these parameters quantitatively represent the intrinsic characteristics of EVH and SARVH and therefore allow the comparison of TTFields in different patients.

Our TTFields modeling is based on MP-RAGE, T1 and T2 MRI sequences obtained from a patient with glioblastoma in the right parietal brain. Using patient-based MRI for finite element modeling has several distinct advantages compared to modeling based on atlas-based human head. First, there are intrinsic factors that are unique to the individual human head that may influence the electric field and specific absorption rate in the GTV. A prime example is the thickness of the cerebrospinal fluid within the subarachnoid space at the convexity. Because cerebrospinal fluid is a conductor, a thicker layer tends to shunt TTFields away from the brain while a thinner layer allows more of the fields to penetrate the brain and eventually to the GTV. Indeed, as brain atrophy occurs in the general population spanning the entire age continuum in adulthood, there is a simultaneous increase in cerebrospinal fluid space from age 18 to 80. Furthermore, the rate of atrophy is quicker for men than woman, particularly in the left hemisphere, suggesting gender and neuroanatomical differences between genders. Second, the presence or absence of the necrosis within the glioblastoma also can influence the distribution of TTFields at the GTV. The necrotic core is primarily represented by thick collection of fluid from broken down cellular debris containing various proteins and metabolites. Because this fluid is ionic and probably highly conductive, it may focus electric fields toward the more cellular portion of the GTV. Indeed, our modeling has shown that the necrotic core can influence both the electric field strength and SAR within the adjacent GTV as the conductivity of GTV varied from 100 to 1 S/m. Lastly, glioblastoma is an infiltrative tumor and the accumulation of the tumor cells in the adjacent gyri and sulci may change the geometry of the tumor. Our geometric analysis has shown that electric field and SAR values grossly increase as the tumor geometry becomes more angulated, as seen in cube and icosahedron compared to spherical and cylindrical shapes. An extreme form of tumor geometric asymmetry is represented by a conical shape and modeling revealed that the orientation of the structure is important, resulting in highest electric field intensity and SAR when the cone is pointing anteriorly and the flat surface of the cone is facing orthogonally to the lateral ventricle. Taken together, atlas-based modeling may not accurately incorporate patient-related differences in age, gender, and physical tumor characteristics, all of which influence TTFields distribution in cancer patients.

The positioning of the transducer arrays also influences TTFields distribution within the brain and/or other anatomical structures. We also determined changes in TTFields at the GTV depending on array positioning, with significant variability in the electric field strength of GTV between 100 to 150 V/m, ranging from only 20% volume having 100 V/m with clockwise rotation of the lateral arrays and no displacement of the anterior-posterior arrays to >40% volume having at least 150 V/m when the lateral arrays are rotated in a counter clockwise fashion and the anterior array is moved backward. SAR variability in the rate of energy deposition is less dramatic, as the magnitude of $SAR_{50\%}$ changes between 3 and 6 W/kg. These results suggest that array positioning is important to maximize TTFields distribution at the GTV and the NovoTAL™ array placement mapping will require validation in the treated patient population.

The modeling described above used isotropic values, but there are local fields generated by the electrical activities of neurons. In some embodiments, anisotropic mapping may delineate the TTFields distribution more accurately. However, for the purpose of comparison of different structural components that may influence TTFields, isotropic modeling may provide for an accurate and/or relative comparison between different personalized array layout, dielectric material properties, geometries, and tumor-related parameters.

Volume histograms EVH and SARVH facilitate comparison between glioblastoma patients undergoing treatment with TTFields. TTFields at the GTV are influenced by the dielectric characteristics of the adjacent tissues as well as the GTV itself, particularly the presence or absence of a necrotic core. The thickness of the cerebrospinal fluid at the convexity of the brain and the geometry of the tumor are also relevant factors. Finally, tumor geometry and the position of the arrays also influence the electric field distribution and rate of energy deposition in the GTV. The method here can also be applied to other anatomical structures in the patient.

Figure 12:
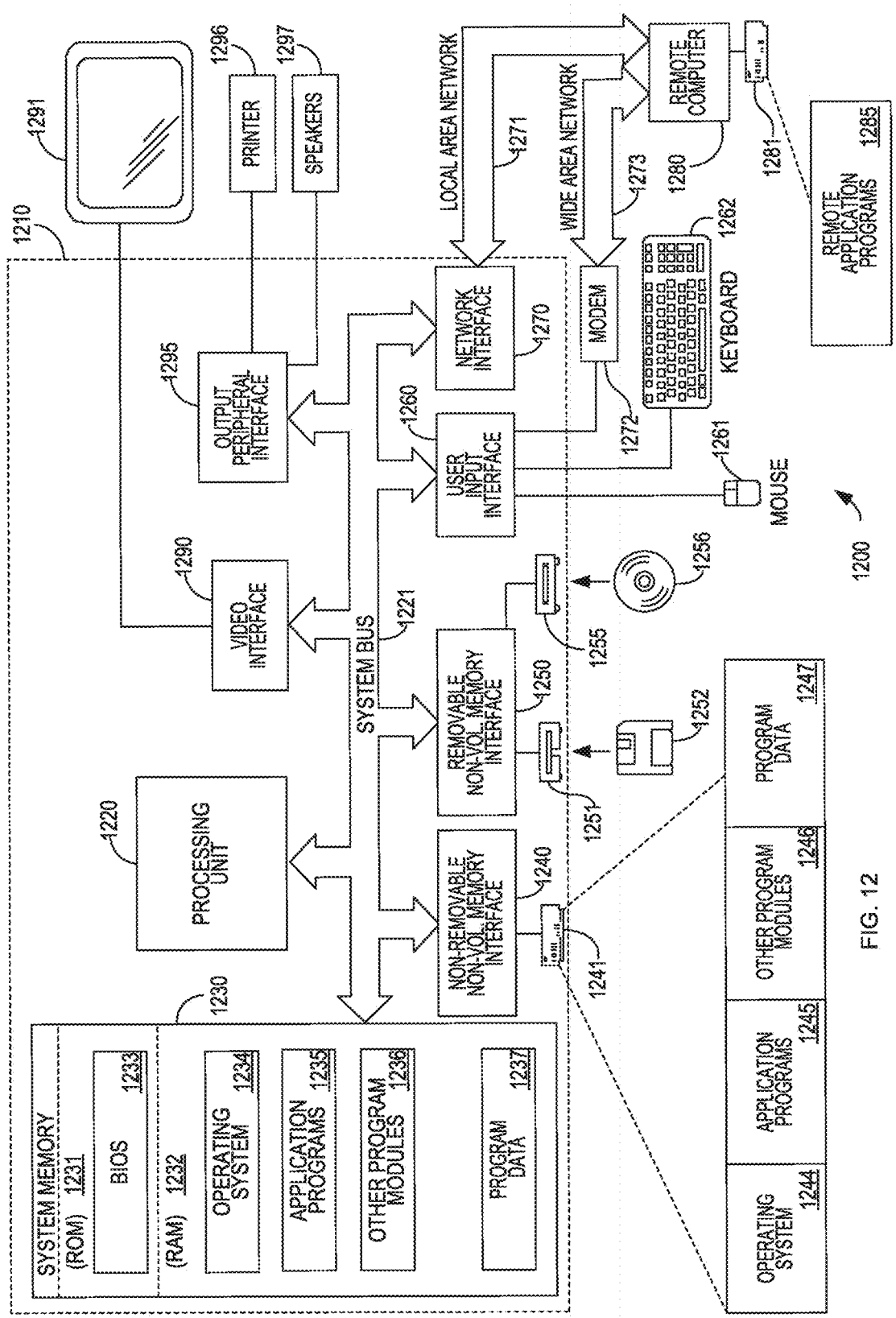
FIG. 12 is a block diagram of an exemplary computer system on which some embodiments may be implemented.

FIG. 12 illustrates an example of a suitable computing system environment 1200 on which the invention may be implemented. The computing system environment 1200 is only one example of a suitable computing environment and is not intended to suggest any limitation as to the scope of use or functionality of the invention. Neither should the computing environment 1200 be interpreted as having any dependency or requirement relating to any one or combination of components illustrated in the exemplary operating environment 1200.

The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, cloud-based systems, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 12, an exemplary system for implementing the invention includes a general purpose computing device in the form of a computer 1210. Components of computer 1210 may include, but are not limited to, a processing unit 1220, a system memory 1230, and a system bus 1221 that couples various system components including the system memory to the processing unit 1220. The system bus 1221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1210 typically includes a variety of computer readable media. Computer readable media can be any available media that can be accessed by computer 1210 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1210. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1230 includes computer storage media in the form of volatile and/or nonvolatile memory such as read only memory (ROM) 1231 and random access memory (RAM) 1232. A basic input/output system 1233 (BIOS), containing the basic routines that help to transfer information between elements within computer 1210, such as during start-up, is typically stored in ROM 1231. RAM 1232 typically contains data and/or program modules that are immediately accessible to and/or presently being operated on by processing unit 1220. By way of example, and not limitation, FIG. 12 illustrates operating system 1234, application programs 1235, other program modules 1236, and program data 1237.

The computer 1210 may also include other removable/non-removable, volatile/nonvolatile computer storage media. By way of example only, FIG. 12 illustrates a hard disk drive 1241 that reads from or writes to non-removable, nonvolatile magnetic media, a magnetic disk drive 1251 that reads from or writes to a removable, nonvolatile magnetic disk 1252, and an optical disk drive 1255 that reads from or writes to a removable, nonvolatile optical disk 1256 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1241 is typically connected to the system bus 1221 through an non-removable memory interface such as interface 1240, and magnetic disk drive 1251 and optical disk drive 1255 are typically connected to the system bus 1221 by a removable memory interface, such as interface 1250.

The drives and their associated computer storage media discussed above and illustrated in FIG. 12, provide storage of computer readable instructions, data structures, program modules and other data for the computer 1210. In FIG. 12, for example, hard disk drive 1241 is illustrated as storing operating system 1244, application programs 1245, other program modules 1246, and program data 1247. Note that these components can either be the same as or different from operating system 1234, application programs 1235, other program modules 1236, and program data 1237. Operating system 1244, application programs 1245, other program modules 1246, and program data 1247 are given different numbers here to illustrate that, at a minimum, they are different copies. A user may enter commands and information into the computer 1210 through input devices such as a keyboard 1262 and pointing device 1261, commonly referred to as a mouse, trackball or touch pad. Other input devices (not shown) may include a microphone, joystick, game pad, satellite dish, scanner, or the like. These and other input devices are often connected to the processing unit 1220 through a user input interface 1260 that is coupled to the system bus, but may be connected by other interface and bus structures, such as a parallel port, game port or a universal serial bus (USB). A monitor 1291 or other type of display device is also connected to the system bus 1221 via an interface, such as a video interface 1290. In addition to the monitor, computers may also include other peripheral output devices such as speakers 1297 and printer 1296, which may be connected through a output peripheral interface 1295.

The computer 1210 may operate in a networked environment using logical connections to one or more remote computers, such as a remote computer 1280. The remote computer 1280 may be a personal computer, a server, a router, a network PC, a peer device or other common network node, and typically includes many or all of the elements described above relative to the computer 1210, although only a memory storage device 1281 has been illustrated in FIG. 12. The logical connections depicted in FIG. 12 include a local area network (LAN) 1271 and a wide area network (WAN) 1273, but may also include other networks. Such networking environments are commonplace in offices, enterprise-wide computer networks, intranets and the Internet.

When used in a LAN networking environment, the computer 1210 is connected to the LAN 1271 through a network interface or adapter 1270. When used in a WAN networking environment, the computer 1210 typically includes a modem 1272 or other means for establishing communications over the WAN 1273, such as the Internet. The modem 1272, which may be internal or external, may be connected to the system bus 1221 via the user input interface 1260, or other appropriate mechanism. In a networked environment, program modules depicted relative to the computer 1210, or portions thereof, may be stored in the remote memory storage device. By way of example, and not limitation, FIG. 12 illustrates remote application programs 1285 as residing on memory device 1281. It will be appreciated that the network connections shown are exemplary and other means of establishing a communications link between the computers may be used.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases.

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. An apparatus comprising:
  circuitry configured to:
    construct, based on at least one image, a representation of a subject's head, the representation including information for a plurality of structures within the subject's head, the plurality of structures including at least one tumor positioned within the subject's brain;
    calculate, using the representation of the subject's head, a plurality of volumetric alternating electric field propagation distributions for a plurality of transducer arrangements of an array of transducers on a surface of the subject's head;
    determine, based on the plurality of volumetric alternating electric field propagation distributions for the plurality of transducer arrangements and the plurality of structures within the subject's head, a plurality of volumetric rate of energy absorption distributions for the plurality of transducer arrangements, wherein each of the plurality of volumetric rate of energy absorption distributions indicates a rate of energy absorbed in a volume comprised of the at least one tumor; and generate, based on the plurality of volumetric rate of energy absorption distributions, an indication of how to place a transducer arrangement, corresponding to a desired volumetric rate of energy absorption distribution, relative to the subject's head to enable the volume comprised of the at least one tumor to be exposed to an alternating electric field having a desired volumetric rate of energy absorption; and a user interface configured to present, to a user, the indication of how to place the transducer arrangement relative to the subject's head.

2. The apparatus of claim 1, wherein the representation of the subject's head includes at least one structure proximate to the at least one tumor.

3. The apparatus of claim 2, wherein the at least one structure includes an intracranial structure.

4. The apparatus of claim 2, wherein the at least one structure includes an artificial structure introduced into the subject's head.

5. The apparatus of claim 4, wherein the artificial structure includes an implantable electrode configured to emit an electric field.

6. The apparatus of claim 4, wherein the artificial structure includes a modulator configured to be positioned between the transducer arrangement and the at least one tumor.

7. The apparatus of claim 6, wherein the modulator is a passive modulator.

8. The apparatus of claim 6, wherein the modulator is an active modulator.

9. The apparatus of claim 1, wherein the representation of the subject's head includes positional information for the plurality of structures.

10. The apparatus of claim 1, wherein the representation of the subject's head includes one or more values for at least one material property for the plurality of structures.

11. The apparatus of claim 10, wherein the at least one material property includes electric conductivity, relative permittivity, thermal conductivity, heat capacity, physical density, and/or Young's modulus.

12. The apparatus of claim 10, wherein the at least one material property includes at least one isotropic dielectric property and/or at least one anisotropic dielectric property.

13. The apparatus of claim 12, wherein the circuitry is further configured to receive at least one image obtained by diffusion tensor imaging and determine the at least one anisotropic dielectric property based on the at least one image obtained by diffusion tensor imaging.

14. The apparatus of claim 1, wherein the circuitry is configured to determine, for each of the plurality of volumetric rate of energy absorption distributions, a rate of energy absorption in the volume comprised of the at least one tumor.

15. The apparatus of claim 1, wherein the circuitry is configured to determine, for each of the plurality of volumetric rate of energy absorption distributions, a specific absorption rate distribution.

16. The apparatus of claim 1, wherein the plurality of transducer arrangements have different transducer positions relative to the subject's head.

17. The apparatus of claim 1, wherein the plurality of structures includes a necrotic core within the at least one tumor.

18. The apparatus of claim 1, wherein the plurality of structures includes a resection cavity.

19. The apparatus of claim 1, wherein the information for the plurality of structures includes a thickness of cerebrospinal fluid.

20. The apparatus of claim 1, wherein the information for the plurality of structures includes a volume of at least one of the plurality of structures.

21. The apparatus of claim 1, wherein the information for the plurality of structures includes at least one selected from the group consisting of a volume for white matter, a volume for grey matter, a volume for brain matter, and a volume for cerebrospinal fluid.

22. The apparatus of claim 1, wherein the circuitry is configured to identify volumes for individual structures in the subject's head using the at least one image.

23. The apparatus of claim 22, wherein, to identify the volumes for the individual structures, the circuitry is configured to segregate the at least one image into regions that correspond to each of the plurality of structures and to determine volumes associated with the regions.

24. The apparatus of claim 1, wherein the circuitry is configured to determine the plurality of volumetric rate of energy absorption distributions by determining a volumetric rate of energy absorption for each of the plurality of structures individually.

25. The apparatus of claim 24, wherein the circuitry is configured to generate, for at least one of the plurality of transducer arrangements, an amount of energy absorption for individual structures of the plurality of structures based on the plurality of volumetric rate of energy absorption distributions.

26. The apparatus of claim 1, wherein the circuitry is configured to identify at least one transducer arrangement from among the plurality of transducer arrangements as having a highest amount of energy absorption at the at least one tumor.

27. The apparatus of claim 1, wherein the circuitry is configured to:
determine, for a first transducer arrangement of the plurality of transducer arrangements, a first amount of energy absorption at the at least one tumor;
determine, for a second transducer arrangement of the plurality of transducer arrangements, a second amount of energy absorption at the at least one tumor; and
identify the first transducer arrangement or the second transducer arrangement as the transducer arrangement corresponding to the desired volumetric rate of energy absorption distribution based on a comparison of the first amount of energy absorption to the second amount of energy absorption.

28. The system of claim 1, wherein the circuitry determines the plurality of volumetric alternating electric field propagation distributions for the plurality of transducer arrangements using different values for one or more of the plurality of structures.

29. A system comprising:
an array of transducers configured to emit an alternating electric field;
circuitry configured to:
construct, based on at least one image, a representation of a subject's head, the representation including information for a plurality of structures within the subject's head, the plurality of structures including at least one tumor positioned within the subject's brain;

calculate, using the representation of the subject's head, a plurality of volumetric alternating electric field propagation distributions for a plurality of transducer arrangements of the array of transducers on a surface of the subject's head;

determine, based on the plurality of volumetric alternating electric field propagation distributions for the plurality of transducer arrangements and the plurality of structures within the subject's head, a plurality of volumetric rate of energy absorption distributions for the plurality of transducer arrangements, wherein each of the plurality of volumetric rate of energy absorption distributions indicates a volumetric rate of energy absorbed in a volume comprised of the at least one tumor; and generate, based on the plurality of volumetric rate of energy absorption distributions, an indication of how to place a transducer arrangement, corresponding to a desired volumetric rate of energy absorption distribution, relative to the subject's head to enable the volume comprised of at least one tumor to be exposed to an alternating electric field having the desired volumetric rate of energy absorption; and a user interface configured to present, to a user, the indication of how to place the transducer arrangement relative to the subject's head.

30. The system of claim 29, wherein the alternating electric field has a frequency between 100 kHz and 300 kHz.

31. A method comprising:

constructing, based on at least one image, a representation of a subject's head, the representation including information for a plurality of structures within the subject's head, the plurality of structures including at least one tumor positioned within the subject's brain;

calculating, using the representation of the subject's head, a plurality of volumetric alternating electric field propagation distributions for a plurality of transducer arrangements of an array of transducers on a surface of the subject's head;

determining, based on the calculating plurality of volumetric alternating electric field propagation distributions for the plurality of transducer arrangements and the plurality of structures within the subject's head, a plurality of volumetric rate of energy absorption distributions for the plurality of transducer arrangements, wherein each of the plurality of volumetric rate of energy absorption distributions indicates a volumetric rate of energy absorbed in a volume comprised of the at least one tumor;

generating, based on the plurality of volumetric rate of energy absorption distributions, an indication of how to place a transducer arrangement, corresponding to a desired volumetric rate of energy absorption distribution, relative to the subject's head to enable the volume comprised of the at least one tumor to be exposed to an alternating electric field having a desired rate of energy absorption; and outputting the indication of how to place the transducer arrangement relative to the subject's head.

\* \* \* \* \*

UNITED STATES PATENT AND TRADEMARK OFFICE
CERTIFICATE OF CORRECTION

PATENT NO. : 11,446,487 B2
APPLICATION NO. : 16/335920
DATED : September 20, 2022
INVENTOR(S) : Eric T. Wong et al.

Page 1 of 1

It is certified that error appears in the above-identified patent and that said Letters Patent is hereby corrected as shown below:

In the Claims

In Claim 31, at Column 32, Line 12:
"based on the calculating plurality"
Should read:
-- based on the plurality --

Signed and Sealed this
Twentieth Day of December, 2022

Katherine Kelly Vidal
*Director of the United States Patent and Trademark Office*